United States Patent [19]

Yamada et al.

[11] Patent Number: 4,906,669

[45] Date of Patent: Mar. 6, 1990

[54] ISOPRENOID DERIVATIVES AND ANTI-ULCER AGENTS CONTAINING THE SAME

[75] Inventors: Kazuhiko Yamada, Ohi; Yoshiyuki Tahara, Tsurugashima; Masashi Toyoda, Kawagoe; Osamu Irino, Tokyo; Noriyuki Misaki, Inagi, all of Japan

[73] Assignees: Nisshin Flour Milling Co., Ltd.; Grelan Pharmaceutical Co., Ltd., both of Japan

[21] Appl. No.: 234,895

[22] Filed: Aug. 22, 1988

[30] Foreign Application Priority Data

Aug. 25, 1987 [JP] Japan ................. 62-209214
Apr. 21, 1988 [JP] Japan ................. 63-96770

[51] Int. Cl.⁴ .................. A01N 37/02; C07C 33/34
[52] U.S. Cl. .................. 514/733; 514/764; 568/715; 568/716
[58] Field of Search ............. 514/453, 675, 925, 926, 514/927, 928, 690, 732, 733, 734, 764; 549/406; 568/376, 716, 734, 804, 811, 813

[56] References Cited

U.S. PATENT DOCUMENTS

| | | | |
|---|---|---|---|
| 3,875,163 | 4/1975 | Zumin et al. | 514/925 |
| 3,928,421 | 12/1975 | Kyogoku et al. | 514/927 |
| 4,353,979 | 10/1982 | Terada et al. | 430/372 |
| 4,393,075 | 7/1983 | Terao et al. | 514/675 |
| 4,436,752 | 3/1984 | Christidis et al. | 514/926 |

FOREIGN PATENT DOCUMENTS 2404621  1/1974  Fed. Rep. of Germany .
2259822  6/1974  France .

OTHER PUBLICATIONS

Preparation of Substituted 6-Hydroxychromans Using Potassium Nitroso Disulfonate Svishchuk et al., Chem. Abs. 83:9690 (1975).
Polyprenyl Derivatives from the Sponge Ircinia Spinosula Cimino et al., Tetrahedron 28:1315-1324 (1972).
Synthesis of 2-Multiprenylphenols and 2-Multiprenyl-6-Methoxyphenols, Biosynthesis Precursors of the Ubiquinones Daves et al., J. Orig. Chem. 32:1414–1417 (1967).
Chemistry Letters, pp. 831–832 (1979).
Reynolds et al., "Prenylated Hydroquinones", Phytochemistry, vol. 20, No. 6, pp. 1365–1366 (1981).
Stevens et al., "The Structure and Synthesis of Alliodorin" Tetrahedron, vol. 32, pp. 665–668 (1976).
Inouye et al., "Zur Struktur des Pirolatins", Chem. Ber., vol. 101, 4057–4065 (1968).
Ochi et al., "Isolation of 2-(3,77,11-Trimethyl-2,6,10-Dodecatrienyl Hydroquinone from the Brown Seaweed Dictyoperis Undulata Chemistry/Lett.", pp. 831–832 (1979).
Cimino et al., "Polyprenyl Derivatives from the sponge Ircina Spinosula", Tetrahedron, vol. 28, pp. 1315–1324 (1972).
Manners, "The Hydroquinone Terpenoids of Cordia Elaeagnoides", J. Chem. Soc. Perkin Trans. 1, pp. 39–43 (1983).
Dave et al., "A Piscicidal Chromanol and a Chromenol from the Brown Alga Dictyopteris Undulata", Heterocycles, 22, No. 10, 2301-7 (1984).
Asawa et al., "The Synthesis of the Hydrogenated Derivative of Amitenone a Methlenebisbenzoquinone from Suillus Bovinus, Mokuzai Gakkaishi", vol. 17, No. 9, 384–392 (1971).
Cimino et al., "Prenylated Quinones in Marine Sponges", Experienta, vol. 28, Fasc. 12, 1401–1402 (1972).

Primary Examiner—H. M. S. Sneed
Assistant Examiner—Jim Saba
Attorney, Agent, or Firm—Abelman Frayne Rezac & Schwab

[57] ABSTRACT

Anti-ulcer agents containing isoprenoid derivatives are provided. The isoprenoid derivatives are represented by the formula:

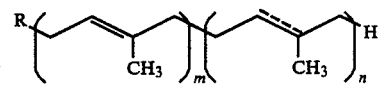

wherein: R represents a group of formula

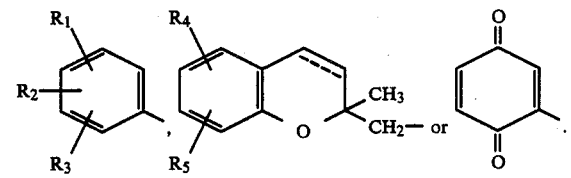

In the above formula, $R_1$, $R_2$ and $R_3$ may be the same or different each other and each represents a hydrogen atom, a hydroxy group, a lower alkanoyloxy group, a lower alkyl group or a lower alkoxy group, provided that two or more of them do not represent hydrogen atoms at the same time; $R_4$ and $R_5$ may be the same or different each other and each represents a hydrogen atom, a hydroxy group or a lower alkanoyloxy group ======represents the signal or the double bond between the carbon atoms; m represents 0 or 1; n represents 0 or an integer of from 1 to 9, provided that the sum of m and n is an integer of from 1 to 9.

6 Claims, No Drawings

ISOPRENOID DERIVATIVES AND ANTI-ULCER AGENTS CONTAINING THE SAME

FIELD OF THE INVENTION

The present invention relates to anti-ulcer agents containing, as an active ingredient, isoprenoid derivatives, particularly those having a phenyl ring, a benzoquinone ring or a benzopyran ring, and to novel isoprenoid derivatives, particularly those having a phenyl ring, a benzoquinone ring or a benzopyran ring which are useful as the anti-ulcer agent.

BACKGROUND OF THE INVENTION

In recent years, ulcers, in particular the peptic ulcer, which is believed to be attributed to various stress, tend to occur with the increase in various social stress factors, such as complicated way of life, increase in the urban population, competitive tendency in the social life, growth of the number of the nuclear families and of the high-aged people, or the like.

Certain chemotherapic agents have been proposed until now for the effective measure of the treatment of the ulcer.

However, none of them may achieve diverse factors all at one to its satisfaction, such as efficacy, safety and economy including production and availability.

OBJECT OF THE INVENTION

Therefore, the present invention is aimed at offering compounds that are useful for anti-ulcer agents which are effective for ulcers, particularly those caused by stress, and which are of high safety and economy, that have not been known in the art.

BRIEF SUMMARY OF THE INVENTION

The invention is to provide anti-ulcer agents containing as the active ingredient certain class of isoprenoid derivatives.

Some of the derivatives are known per se in the art, while the others are new and form themselves part of the invention.

The isoprenoid derivatives, which may be used as the active ingredient for the anti-ulcer agents of the present invention, may be represented by the following formula (I):

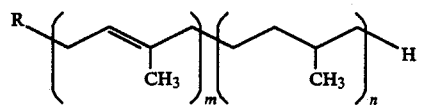
(I)

wherein: R represents a group of formula

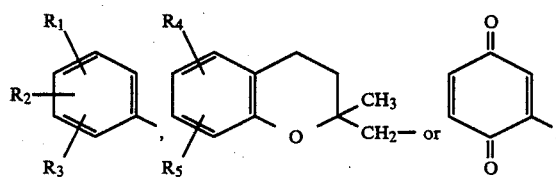

In the above formula, $R_1$, $R_2$, and $R_3$ may be the same or different each other and each represents a hydrogen atom, a hydroxy group, a lower alkanoyloxy group, a lower alkyl group or a lower alkoxy group, provided that two or more of them do not represent hydrogen atoms at the same time; $R_4$ and $R_5$ may be the same or different each other and each represents a hydrogen atom, a hydroxy group or a lower alkanoyloxy group; represents the single or the double bond between the carbon atoms; m represents 0 or 1; n represents 0 or an integer of from 1 to 9, provided that the sum of m and n is an integer of from 1 to 9.

Of the isoprenoid compounds represented by the formula (I), those represented by the following formula (Ia) are new:

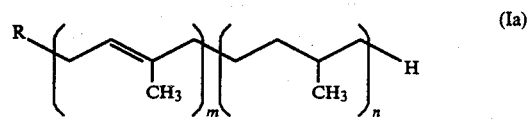
(Ia)

wherein: R represents a group of formula

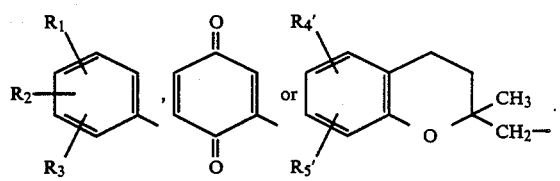

In the above formula, $R_1$, $R_2$ and $R_3$ may be the same or different each other and each represents a hydrogen atom, a hydroxy group, a lower alkanoyloxy group, a lower alkyl group or a lower alkoxy group, provided that two or more of them do not represent hydrogen atoms at the same time; $R_4'$ and $R_5'$ may be the same or different each other and each represents a hydrogen atom or a hydroxy group; represents the single or the double bond between the carbon atoms; m represents 0 or 1; n represents an integer of 3, 4 or 8, provided that represents the single bond when n is 3 and represents the double bond when n is 8.

DETAILED DESCRIPTION OF THE INVENTION

In the above fomulae (I) and (Ia), where $R_1$, $R_2$, $R_3$, $R_4$ and $R_5$ represent the lower alkanoyloxy groups, they may be alkanoyloxy groups having from 2 to 4 carbon atoms, such as acetoxy, propionyloxy, butyryloxy, isobutyryloxy or t-butyryloxy groups.

Where $R_1$, $R_2$ and $R_3$ represent lower alkyl groups, they may be straight or branched chain alkyl groups having from 1 to 6 carbon atoms, such as methyl, ethyl, propyl, isopropyl, butyl, isobutyl, t-butyl, amyl or hexyl groups.

Where $R_1$, $R_2$ and $R_3$ represent lower alkoxy groups, they may be the oxy groups substituted by such alkyl groups as exemplified above.

The compound of the formulae (I) and (Ia) may be prepared by any of the following methods:

(1) Hydroquinone or a substituted benzene and a polyprenyl alcohol is allowed to react in a suitable solvent in the presence of a protonic acid or a Lewis acid to give a condensation product which, in turn, is allowed to react with an acrylating agent to introduce a lower alkanoyl group.

(2) The condensation product obtained in (1) above is treated with an oxidizing agent.

(3) The reaction product obtained in (2) is further reacted in a suitable solvent in the presence of an alkaline catalyst.

The polyprenyl alcohols, which are the starting materials in these reactions, may be used as such, or in the form of functional derivatives such as polyprenyl halides (e.g. polyprenyl fluoride, polyprenyl chloride, polyprenyl bromide or polyprenyl iodide) or esters of the polyprenyl alcohols (e.g. polyprenyl acetate, polyprenyl propionate or polyprenyl sulfate).

The substituted benzenes include, for example, alkylphenols (e.g. 2,6-di-t-butylphenol), polyphenols (e.g. dihydroxy-benzenes such as 1,2-benzenediol or trihydroxybenzenes such as 1,2,3-benzenetriol) and alkoxybenzenes (e.g. 1,2-dimethoxybenzene).

The proportion of the hydroquinone or the substituted benzene to the polyprenyl alcohol or the functional derivative thereof is not critical. Normally, they are used in a molar ratio of between 0.1:1.0 and 1.0:0.1, preferably between 1.0:1.0 and 1.0:0.3, more preferably between 1.0:0.4 and 1.0:0.6.

There is no particular limitation in the nature of the solvents used in the condensation reaction of the hydroquinone or the substituted benzene with the polyprenyl alcohol or the functional derivative thereof, as far as they do not adversely interfere with the reaction. They include, for example, aliphatic hydrocarbons such as hexane or petroleum ether, aromatic hydrocarbons such as benzene, toluene or xylene, cycloaliphatic hydrocarbons such as cyclohexane, halohydrocarbons such as carbon tetrachloride, chloroform, ethylene dichloride or trichloroethylene, cyclic ethers such as dioxane or tetrahydrofuran, aliphatic esters such as ethyl acetate or butyl acetate, aliphatic ketones such as acetone or methyl ethyl ketone, pyridine, N,N-dimethylformamide and dimethyl sulfoxide.

The protonic acids as the catalyst include, for example, mineral acids such as hydrochloric acid, sulfuric acid or phosphoric acid and organic acids such as p-toluenesulfonic acids, and organic acids such as p-toluenesulfonic acid while the Lewis acids include, for example, boron trifluoride ethyl etherate, zinc chloride or aluminum chloride.

In the condensation reaction described above, where the group R denotes the substituted phenyl group, the reaction is advantageously effected in dioxane in the presence of boron trifluoride ethyl etherate, whereby the target compound may be obtained as the major product.

Where the group R denotes the benzopyranyl group, the reaction is advantageously effected in butyl acetate in the presence of zinc chloride, whereby the target compound may be obtained as the major product. Alternatively, the reaction is advantageously effected in dioxane in the presence of boron triluoride ethyl etherate to give a reaction product which, in turn, is treated with an acid in the presence of a solvent. The acids include, for example, mineral acids such as hydrochloric acid or sulfuric acid, or organic acids such as p-toluenesulfonic acid. The solvents include, for example, alcohols such as methanol or ethanol, aliphatic hydrocarbons such as hexane or petroleum ether, aromatic hydrocarbons such as benzene, toluene or xylene, cycloaliphatic hydrocarbons such as cyclohexane, halohydrocarbons such as carbon tetrachloride, chloroform, ethylene dichloride or trichloroethylene, cyclic ethers such as dioxane or tetrahydrofuran, aliphatic esters such as ethyl acetate or butyl acetate, aliphatic ketones such as acetone or methyl ethyl ketone, N,N-dimethylformamide and dimethyl sulfoxide.

The reaction of the hydroquinone or the substituted benzene with the polyprenyl alcohol may normally be effected at a temperature of from ambient to 200° C., preferably at a temperature of from ambient to the boiling temperature of the solvent used, for the period of about from 1 hour to 24 hours.

When the reaction is in complete, the target compound, that is to say the condensation product, may be recovered by conventional means. For example, the solvent is removed by distillation; water is added to the residue, which is then extracted with a suitable organic solvent such as diethyl ether or ethyl acetate; the solvent is distilled off from the extract by distillation; and the residue is subjected to distillation in vacuo or to recrystallization or chromatography.

In the compounds of the formulae (I) and (Ia), where at least one of $R_1$, $R_2$ and $R_3$ are alkanoyloxy groups, the compounds obtained by the condensation reaction in which at least one of $R_1$, $R_2$ and $R_3$ are the hydroxy groups are further reacted with an aliphatic carboxylic acid having from 2 to 4 carbon atoms or the reactive derivatives thereof such as the acid anhydrides or the acid halides (e.g. acid chloride or acid bromide).

Where the aliphatic carboxylic acid is used as such, the reaction may preferably be carried out in the presence of a dehydrating agent such as a mineral acid (e.g. hydrochloric acid or sulfuric acid, or an organic acid (e.g. p-toluenesulfonic acid). Where an acid halide is used, the reaction may preferably be carried out in the presence of a base such as an inorganic base (e.g. potassium hydroxide, sodium hydroxide, potassium carbonate or sodium carbonate) or an organic base (e.g. a teritary amine such as triethylamine or tributylamine, or pyridine).

The acylation reaction is suitably carried out in a solvent.

Such solvents include, for example, aliphatic hydrocarbons such as hexane or petroleum ether, aromatic hydrocarbons such as benzene, toluene or xylene, cycloaliphatic hydrocarbons such as cyclohexane, halohydrocarbons such as carbon tetrachloride, chloroform, ethylene dichloride or trichloroethylene, cyclic ethers such as dioxane or tetrahydrofuran, aliphatic esters such as ethyl acetate or butyl acetate, aliphatic ketones such as acetone or methyl ethyl ketone, pyridine, N,N-dimethylformamide and dimethyl sulfoxide.

The reaction may normally be effected at a temperature of from ambient to 200° C., preferably at a temperature of from ambient to the boiling temperature of the solvent used, for the period of about from 1 hour to 24 hours.

When the reaction is in complete, the solvent is distilled off from the reaction mixture, the residue is extracted, and the desired product may be purified by such conventional means as recrystallization, distillation in vacuo or chromatography.

The compounds of formulae (I) and (Ia), in which R is the benzoquinonyl group, may be obtained by reacting the condensation product obtained as above with a suitable oxidizing agent.

The oxidizing agents include, for example, lead tetraacetate, lead dioxide, nitric acid, silver oxide and silver carbonate/celite.

The reaction is suitably carried out in a solvent. Such solvents include, for example, aliphatic hydrocarbons such as hexane or petroleum ether, aromatic hydrocarbons such as benzene, toluene or xylene, cycloaliphatic hydrocarbons such as cyclohexane, halohydrocarbons such as carbon tetrachloride, chloroform, ethylene dichloride or trichloroethylene, cyclic ethers such as dioxane or tetrahydrofuran, aliphatic esters such as ethyl acetate or butyl acetate, aliphatic ketones such as acetone or methyl ethyl ketone, pyridine, N,N-dimethylformamide and dimethyl sulfoxide.

Alternatively, other types of oxidizing agents such as sodium bichromate, sodium chlorate or ferric chloride may be used. In this case, the oxidation reaction is conveniently carried out in a suitable acidic medium such as dilute sulfuric acid or dilute hydrochloric acid.

The reaction may normally be effected at a temperature of from ambient to 200° C., preferably at a temperature of from ambient to the boiling temperature of the solvent used, for the period of about from 1 hour to 24 hours.

When the reaction is in complete, insoluble impurities are removed from the reaction mixture by filtration, the filtrate is poured into water and extracted with a suitable solvent, and the desired product may be purified by such conventional means as recrystallization, distillation in vacuo or chromatography.

Of the compounds of the formula (I), the chromenol compounds may be obtained by treating the benzoquinone compounds as prepared above with a base in a suitable solvent.

Such solvents include, for example, aliphatic hydrocarbons such as hexane or petroleum ether, aromatic hydrocarbons such as benzene, toluene or xylene, cycloaliphatic hydrocarbons such as cyclohexane, halohydrocarbons such as carbon tetrachloride, chloroform, ethylene dichloride or trichloroethylene, cyclic ethers such as dioxane or tetrahydrofuran, aliphatic esters such as ethyl acetate or butyl acetate, aliphatic ketones such as acetone or methyl ethyl ketone, pyridine, N,N-dimethylformamide and dimethyl sulfoxide.

The bases include, for example, inorganic bases (e.g. potassium hydroxide, sodium hydroxide, potassium carbonate or sodium carbonate) or organic bases (e.g. a tertiary amine such as triethylamine or tributylamine, or pyridine).

The reaction may normally be effected at a temperature of from ambient to 200° C., preferably at a temperature of from ambient to the boiling temperature of the solvent used, for the period of about from 1 hour to 24 hours.

When the reaction is in complete, the solvent is distilled off from the reaction mixture, the residue is extracted with a suitable solvent, and the desired product may be purified by such conventional means as recrystallization, distillation in vacuo or chromatography.

The compound of the general formula (I) in which the isoprenoide side chain bonded to R is saturated, is obtainable by the catalytic reduction of the corresponding unsaturated compound.

In this reaction, platinum oxide, palladium on active carbon, palladium on barium sulfate, Raney's nickel etc. is used as a reaction catalyst.

As a reaction solvent, an alcohol such as methanol and ethanol, an aliphatic carboxylic acid, such as acetic acid and propionic acid, a cyclic ether, such as tetrahydrofuran and dioxane, an aliphatic hydrocarbon, such as n-hexane and petroleum ether, an aromatic hydrocarbon, such as benzene, toluene and xylene, an alicyclic compound, such as cyclohexane, and water, is able to use.

This reaction is usually carried out at a temperature of the range from room temperature to 200° C., for a period of from 1 to 48 hours, and under a hydrogen pressure of from atmospheric to 200 atoms.

Upon a completion of the reaction, the purified end product is obtainable by filtering off the catalyst from the reaction mixture, evaporating the solvent from the filtrate, and subjecting the product to such purification steps as extraction, recrystallization, distilling under reduced pressure and chromatography.

Representative compounds which may be prepared and used as the active ingredient of the anti-ulcer agents of the invention will be given below:

2-(3,7,11,15-Tetramethyl-2-hexadecenyl)-1,4-hydroquinone,
2-Methyl-2-(4,8,12-trimethyltridecyl)-6-chromanol,
2-Methyl-2-(4,8,12-trimethyltridecyl)-5-hydroxychromene,
2-Geranyl-1,4-hydroquinone,
2-Geranyl-1,3-hydroquinone,
2-[3,7(R),15-Tetramethyl-2-hexadecenyl]-1,4-hydroquinone,
2-Methyl-2-[4(R),12-trimethyltridecyl]-6-chromanol,
2-Farnesyl-1,4-hydroquinone,
2-Methyl-2-[4(R),12-trimethyltridecyl]-6-chromanol acetate,
2-Methyl-2-[4(R),8(R),12-trimethyltridecyl]-5-acetoxychromene,
2-Methyl-2-[4(R),8(R),12-trimethyltridecyl]-6-t-butoxychromene,
2-Methyl-2-[4(R),8(R),12-trimethyltridecyl]-6-propionyloxychromene,
2-[3,7(R),11(R),15-Tetramethyl-2-hexadecenyl]-1,4-diacetoxybenzene,
2-[3,7(R),11(R),15-Tetramethyl-2-hexadecenyl]-1,4-dibutoxybenzene,
2-Geranylgeranyl-1,4-hydroquinone,
2-(3,7,11,15-Tetramethyl-2-hexadecenyl)-1,4-diacetoxybenzene,
2-(3,7,11,15,19-Pentamethyl-2,6,10,14,18-eicosapentaenyl)-1,4-hydroquinone,
2-(3,7,11,15,19,23-Hexamethyl-2,6,10,14,18,22-tetracosahexaethyl-1,4-hydroquinone,
2-(3,7,11,15,19,23,27-Heptamethyl-2,6,10,14,18,22,26-octacosaheptaenyl)-1,4-hydroquinone,
2-Solanesyl-1,4-hydroquinone,
2,6-Dimethyl-4-(3,7,11,15-tetramethyl-2-hexadecenyl)-phenol,
2,6-Di-t-butyl-4-(3,7,11,15-tetramethyl-2-hexadecenyl)-phenol,
2-Methyl-4-(3,7,11,15-tetramethyl-2-hexadecenyl)-phenol,
3-(3,7,11,15-Tetramethyl-2-hexadecenyl)-1,2-benzenediol,
4-(3,7,11,15-Tetramethyl-2-hexadecenyl)-1,2-benzenediol,
4-(3,7,11,15-Tetramethyl-2-hexadecenyl)-1,2-dimethoxybenzene,
4-(3,7,11,15-Tetramethyl-2-hexadecenyl)-1,2-3-benzenetriol,
2-Methyl-2-(4-methyl-3-pentenyl)-6-chromenol,
2-Methyl-2-(4-methyl-3-pentenyl)-5-hydroxychromene,
2-Methyl-2-(4,8-dimethyl-3,7-nonadienyl)-6-chromenol,
2-Methyl-2-(4,8,12-trimethyl-3,7,11-tridecatrienyl)-6-chromenol,
2-(3,7,11,15-Tetramethyl-2-hexadecenyl)-1,4-benzoquinone, 2-[3,7(R),11(R),15-Tetramethyl-2-hexadecenyl]-1,4-benzoquinone,
4-(3,7,11,15-Tetramethyl-2-hexadecenyl)-1,3-diacetoxybenzene,
4-(3,7,11,15-Tetramethyl-2-hexadecenyl)-1,3-benzenediol,
2-(3,7,11,15-Tetramethyl-2-hexadecenyl)-1,3,5-triacetoxybenzene,
2-(3,7,11,15-Tetramethyl-2-hexadecenyl)-1,3,5-benzenetriol,
4-(3,7,11,15-Tetramethyl-2-hexadecenyl)-1,2,3-triacetoxybenzene,
2-Methyl-2-(4,8,12-trimethyltridecyl)-7-chromanol,
2-Methyl-2-(4,8,12-trimethyltridecyl)-7,8-dichromanol,
2-Methyl-2-(4,8,12-trimethyltridecyl)-5,7-dichromanol,
2-Methyl-2-(4,8,12-trimethyltridecyl)-8-chromanol,
3-(3,7,11,15-Tetramethyl-2-hexadecenyl)-1,2-diacetoxybenzene,
4-(3,7,11,15-Tetramethyl-2-hexadecenyl)-1,2-diacetoxybenzene,
2-(3,7,11,15-Tetramethylhexadecenyl)-1,4-hydroquinone,
4-(3,7,11,15-Tetramethylhexadecenyl)-1,3-benzenediol.

The compounds prepared and used in this invention include one or more asymmetric carbon atoms. Any substituents attached to those carbon atoms may take either R- or S-form. Therefore, individual optical isomers as well as racemic mixtures of these isomers are included within the scope of this invention.

The compounds represented by the formulae (I) and (Ia) exhibit anti-ulcer activity in mammalian animals such as humans, monkeys, cats, rabbits, rats and mice. Accordingly, they are useful as the preventive or curative anti-ulcer agents, in particular those for the treatment of the peptic ulcer. For example, they are useful for the treatment of the psychogenic peptic ulcer caused by external stimula or stress, or of the peptic ulcer caused by drugs, foods and alcoholic drinks.

The compounds of this invention are useful as the preventive or curative anti-ulcer agents at various sites of the digestive organs, such as the gullet, the stomach, the duodenum, the small intestine and the large intestine.

The compounds of this invention may be used either alone or in combination. They may be used together with known anti-ulcer agents. The compounds of this invention may be administered either orally or parenterally. Normally, one or more active ingredients are formulated into various forms of preparations in combination with additives which are pharmaceutically acceptable. The amount of the compound of this invention in the final dosage form will normally be in a range of from 0.01 to 30% by weight, preferably from 0.05 to 20% by weight.

The additives which are commonly and conventionally used in the art are described, for example, in A. O. Chairman et al, "Remington's Pharmaceutical Science", 1980 Edition, Mack Publishing Co. The nature and the kind of the additives differ, depending on the route of administration and the type of preparation, such as oral preparations (e.g. tablets, syrups or liquids), injectable solutions (e.g. intravenous injections, subcutaneous injections or intramuscular injections), mucosal preparations (e.g. buccal tablets, trochisci or suppositories) and pellicular preparations (e.g. ointments or cataplasms).

For oral and mucosal preparations, excipients (e.g. starch or lactose), disintegrating agents (e.g. carboxymethylcellulose), lubricants (e.g. magnesium stearate), coating agents (e.g. hydroxyethylacellulose) or masking agents may be used. For injectable solutions, solvents or solubilizing agents that are the constituents of the aqueous preparations (e.g. distilled water, physiological saline or propylene glycol), suspending agents (e.g. surface active agents such as polysorbate 80), pH adjusting agents (e.g. organic acids and their metallic salts) or stabilizers may be used. For pellicular preparations, aqueous or oily solvents or solubilizing agents (e.g. alcohols or fatty acid esters), sticking agents (e.g. carboxy vinyl polymers or polysaccharides) or emulsifiers (e.g. surface active agents) may be used.

There is no limitation as to the method of manufacturing the preparations, as long as the objects of the present invention are not disturbed. For example, they may be prepared in accordance with the descriptions of The Pharmacopoeia of Japan, 10th Edition. Alternatively, any other means or methods used in other field of technology, such as foods and confectionaries, or any alterations or modifications of those means and methods may be employed.

The dosage of the compounds of the present invention may differ, depending upon various factors such as the type of disease, the degree of symptom, the age of patient, sex or body weight, etc. Normally, in the case of the oral or pellicular preparations, the compound of this invention may be administered in a dosage of from 50 mg to 5 g per day, preferably from 100 mg to 3 g per day, once or in the divided dosages of from 2 to 4 times. In the case of mucosal preparations, the dosage will range from about 1/5 times to the same amount as that of the oral or pellicular preparations. In the case of the injectable solutions, the dosage will range from about 1/20 to ½ times as that of the oral or pellicular preparations.

The invention is illustrated by the following working examples, test examples and preparative examples.

The compounds or pharmaceuticals according to the present invention will hereunder be explained in more detail with reference to the following non-limitative examples, test examples and illustrative formulations.

EXAMPLE 1

2-(3,7,11,15-Jetramethyl-2-hexadecenyl)-1,4-hydroquinone (Compound 1)

To 11.0 g (100 mmole) of 1,4-hydroquinone and 5.68 g (40 mmole) of boron trifluoride ethyl etherate in 100 ml of dioxane there was dropwise added, at 40° C., 14.8 g (50.0 mmole) of 3,7,11,15-tetramethyl-2-hexadecen-1-ol in 30 ml of dioxane over one hour. After stirring the solution at that temperature for 30 minutes, the reaction solution was poured into water (500 ml) and then extracted twice with ether (500 ml). The extract was successively washed with 700 ml of 5% (w/v) aqueous sodium hydroxide solution (one time), 700 ml of water (two times) and then 700 ml of saturated aqueous sodium chloride solution (one time), followed by drying over anhydrous magnesium sulfate, evaporating off the solvent therefrom and thereafter subjecting the resultant residue to silica gel column chromatography (eluent:hexane-ethyl acetate (3:1). Thus, 8.86 g (22.8 mmole) of the title compound (1) was obtained from the eluted fractions (yield=46%).

$^1$H NMR (200 MHz, CDCl$_3$) : δ=0.8–0.9(12H,m), 1.0–1.7(19H,m), 1.74(3H,s), 1.9–2.1(2H,m), 3.30(2H,d,J=7.1 Hz), 4.57(1H,s), 4.83(1H,s), 5.28(1H,s), 6.5–6.7(3H,m).

IRv $_{max}$cm−1 (neat) =3370; 2950; 2920; 2860; 1500;1460.

EXAMPLE 2

2-Methyl-2-(4,8,12-trimethyltridecyl)-6-chromanol (Compound 2)

To 1.10 g (10.0 mmole) of 1,4-hydroquinone and 409 mg (3.00 mmole) of zinc chloride in 5 ml of butyl acetate there was dropwise added, under nitrogen atmosphere, 1.48 g (5.00 mmole) of 3,7,11,15-tetramethyl-2-hexadecen-1-ol in 5 ml of butyl acetate over one hour while refluxing under heating. After the completion of the dropwise addition, the reaction solution was refluxed under heating for additional 30 minutes, followed by allowing the reaction solution to cool, pouring it into water (100 ml) and extracting it twice with ether (100 ml×1; 50 ml×1). The combined extract was successively washed with 150 ml of 5% (w/v) aqueous sodium hydroxide solution (one time), 150 ml of water (one time) and 150 ml of saturated aqueous solution of sodium chloride (one time), followed by drying over anhydrous magnesium sulfate, distilling off the solvent and subjecting the residue to silica gel column chromatography. Thus, 770 mg (2.0 mmole) of the title compound (2) was recovered from the eluted fractions (eluent:hexane-ethyl acetate (10:1). Yield:40%.

$^1$H NMR (200 MHz, CDCl$_3$) : δ=0.8–1.8(38H,m), 2.69(2H,t,J=6.6 Hz), 4.54(1H,s), 6.5–6.7(3H,m).

IRv $_{max}$cm−1 (neat) =3400; 2950; 2920; 2860; 1500; 1460; 1450; 1220.

EXAMPLE 3

2-Geranyl-1,4-hydroquinone (Compound 3)

A solution of geraniol (2.31 g;15.0 mmole) in dioxane (6 ml) was dropwise added to a solution of 3.30 g (30.0 mmole) of 1,4-hydroquinone and 1.7 g (12 mmole) of boron trifluoride ethyl etherate in 30 ml of dioxane at 50° C. over an hour. After stirring the resultant solution at that temperature for 30 minutes, it was poured into 200 ml of water and then extracted twice with ether (200 ml×1;100 ml×1). After washing, successively with 200 ml of 5% (w/v) aqueous sodium hydroxide solution (one time), 200 ml of water (two times) and 200 ml of saturated aqueous sodium chloride solution (one time), the combined extract was dried over anhydrous magnesium sulfate, the solvent was distilled off and the residue was chromatographed through a silica gel column (eluent=hexane-ethyl acetate (3:1)) to recover 730 mg (3.0 mmole) of the title compound (3) from the eluted fractions (yield=20%).

$^1$H NMR (200 MHz, CDCl$_3$):
δ=1.59(3H,s), 1.68(3H,s), 1.74(3H,s)
2.0–2.1(4H,m), 3.29(2H,d), 4.78(1H,s),
4.89(1H,s), 5.0–5.1(1H,m), 5.2–5.3(1H,m),
6.5–6.7(m,3H).
IRv $_{max}$cm−1 (neat) =3400; 2950; 2920; 2860;
1500; 1460, 1450, 1380,
1220.

EXAMPLE 4

2-[3,7(R),11(R),15-Tetramethyl-2-hexadecenyl]-1,4-hydroquinone (Compound 4)

A solution of 14.8 g (50.0 mmole) of 3, 7(R), 11(R), 15-tetramethyl-2-hexadecen-1-ol in 30 ml of dioxane was dropwise added to a solution of 1,4-hydroquinone (11.0 g;100 mmole) and boron trifluoride ethyl etherate (5.68 g;40 mmole) in 100 ml of dioxane at 40° C. over one hour. After stirring the resultant solution at that temperature for 30 minutes, the reaction solution was poured into 500 ml of water and was extracted two times with ether (500 ml). The extract was successively washed with 700 ml of 5% (w/v) aqueous sodium hydroxide solution (one time) twice with water (700 ml) and then once with saturated aqueous sodium chloride solution (700 ml), followed by drying over anhydrous magnesium sulfate, distilling off the solvent and subjecting the residue obtained to silica gel column chromatography. Thus, the title compound (4) (10.9 g;28.0 mmole) was recovered from the fractions eluted with hexane-ethyl acetate (3:1). Yield=56%.

$^1$H NMR (200 MHz, CDCl$_3$):
δ=0.8–1.7(m,18H), 1.74(s,3H),
1.9–2.1(m,2H), 3.30(2H,d,J=7.3 Hz),
4.60(1H,s), 4.84(1H,s), 5.29(1H,t),
6.5–6.7(3H,m).
IRv $_{max}$cm−1 (neat) =3360, 2950, 2920, 2860
1500, 1460, 1220.

EXAMPLE 5

2-Methyl-2-[4(R),8(R),12-trimethyltridecyl]-6-chromanol (Compound 5)

To a solution of 1,4-hydroquinone (3.30 g;30.0 mmole) and zinc chloride (1.23 g;9.00 mmole) in 17 ml of butyl acetate there was dropwise added a solution of 3,7(R), 11(R),15-tetramethyl-2-hexadecen-1-ol (4.45 g;15.0 mmole) in 7 ml of butyl acetate over one hour, under nitrogen atmosphere while refluxing under heating. After the completion of the dropwise addition, the reaction solution was further refluxed under heating for additional one hour, followed by allowing the refluxed solution to cool, pouring it into 200 ml of water and then extracting it twice with ether (200 ml×1;100 ml×1). The extract was successively washed once with 200 ml of 5% (w/v) aqueous sodium hydroxide solution, twice with water (200 ml) and then once with 200 ml of saturated aqueous sodium chloride solution and was dried over anhydrous magnesium sulfate, followed by distilling off the solvent and thereafter subjecting the resulting residue to silica gel column chromatography to recover 2.80 g (7.20 mmole) of the title compound (5) from the fractions eluted with hexane-ethyl acetate (10:1). Yield =48%

$^1$H NMR (200 MHz, CDCl$_3$):
δ=0.8–1.8(38H,m), 2.69(2H,t,J=7.1 Hz),
4.35(1H,s), 6.5–6.7(3H,m).
IRv $_{max}$cm−1 (neat) =3400, 2950; 2920; 1500;
1460, 1380, 1220.

EXAMPLE 6

2-Farnesyl-1,4-hydroquinone (Compound 6)

A solution of farnesol (5.56 g;25.0 mmole) in dioxane (10 ml) was dropwise added to a solution of 1,4-hydroquinone (5.50 g;50.0 mmole) and boron trifluoride ethyl etherate (2.8 g;20 mmole) in dioxane (50 ml) at 40° C. over one hour. After stirring the reaction solution at that temperature for 30 minutes, the solution was poured into 250 ml of water and then was extracted twice with ether (200 ml). The extract was successively washed once with 5% (w/v) aqueous sodium hydroxide solution (300 ml), twice with water (300 ml) and then once with saturated aqueous sodium chloride solution (300 ml), it was then dried over anhydrous magnesium sulfate, the solvent was distilled off and the residue obtained was chromatographed through a silica gel column. Thus, 2.17 g (6.90 mmole) of the title compound (6) was recovered from the fractions eluted with hexane-ethyl acetate (5:1). Yield=28%.

$^1$H NMR (200 MHz, CDCl$_3$):
δ=1.60(6H,s), 1.68(3H,s), 1.75(3H,s),
1.8-2.2(8H,m), 3.30(2H,d,J=6.8 Hz),
4.53(1H,s), 4.78(1H,s), 5.0-5.1(2H,m)
5.29(1H,t), 6.5-6.7(3H,m).

IRν $^{max}$cm−1 (neat) =3400, 2960, 2920, 1500, 1450, 1200.

EXAMPLE 7

2-Methyl-2-[4(R),8(R),12-trimethyltridecyl]-6-chromanol acetate (Compound 7)

There was dissolved 540 mg (1.4 mmole) of 2-methyl-2-[4(R),8(R),12-trimethyltridecyl]-6-chromanol in 5 ml of pyridine and was added, to the resultant solution, 280 mg (2.7 mmole) of acetic anhydride while ice-cooling. The temperature of the solution was raised up to room temperature, the solvent was removed by distillation after stirring the solution for one hour and the residue obtained was chromatographed through a column packed with silica gel. Thus, 560 mg (1.3 mmol) of the title compound (7) was obtained from the fractions eluted with hexane-ethyl acetate (10:1). Yield=93%.

$^1$H NMR (200 MHz, CDCl$_3$):
δ=0.8-2.0(38H,m), 2.26(3H,s), 2.73(2H,t,J=6.8 Hz), 6.7-6.8(3H,m).

IRν $^{max}$cm−1 (neat) =2940, 2920, 2850, 1760, 1490, 1200.

EXAMPLE 8

2-[3,7(R),11(R),15-Tetramethyl-2-hexadecenyl]-1,4-diacetoxybenzene (Compound 8)

500 mg (1.3 mmole) of 2-[3,7(R),11(R),15-tetramethyl-2-hexadecenyl]-1,4-hydroquinone was dissolved in 5 ml of pyridine and 540 mg (5.3 mmole) of acetic anhydride was added thereto with ice-cooling. The temperature of the reaction solution was brought back to room temperature, the solution was stirred for one hour before the solvent was distilled off and the residue thus obtained was subjected to silica gel column chromatography to recover 550 mg (1.2 mmol) of the title compound (8) from the fractions eluted with hexane-ethyl acetate (10:1) in a 90% yield.

$^1$H NMR (200 MHz, CDCl$_3$):
δ=0.8-2.0(36H,m), 2.27(3H,s), 2.29(3H,s),
3.22(2H,d,J=7.3 Hz), 5.2-5.3(1H,m),
6.9-7.0(3H,m).

IRν $^{max}$cm−1 (neat) =2950, 2930, 2870, 1770, 1500, 1370, 1210, 1180.

EXAMPLE 9

2-Geranylgeranyl-1,4-hydroquinone (Compound 9)

A solution of 7.26 g (25.0 mmole) of geranyllinalool in 20 ml of dioxane was dropwise added to a solution of 1,4-hydroguinone (5.50 g;50.0 mmole) and boron trifluoride ethyl etherate (2.8 g;20 mmole) in 50 ml of dioxane at a temperature of 50° C. over one hour. The mixed solution was stirred at that temperature for 1.5 hours, was poured into 250 ml of water and was extracted twice with ether (200 ml). The extract was successively washed once with 5% (w/v) aqueous sodium hydroxide solution (300 ml), twice with water (300 ml) and once with saturated aqueous sodium chloride solution (300 ml), was dried over anhydrous magnesium sulfate, followed by removing the solvent by distillation and subjecting the resultant residue to a silica gel column chromatography to obtain 3.36 g (8.78 mmole) of the title compound (9) from the fractions eluted with hexane-ethyl acetate (3:1) in an yield of 35%.

$^1$H NMR (200 MHz, CDCl$_3$):
δ=1.59(9H,s), 1.68(3H,s), 1.75(3H,s),
2.0-2.2(12H,m), 3.30(2H,d), 4.64(1H,s),
4.83(1H,s), 5.0-5.2(3H,m), 5.2-5.4(1H,m),
6.5-6.7(3H,m).

IRν $^{max}$cm−1 (neat) =3380, 2960, 2920, 2850, 1500, 1450, 1200.

EXAMPLE 10

2-(3,7,11,15-tetramethyl-2-hexadecenyl)-1,4-diacetoxybenzene (Compound 10)

The same procedures as in Example 8 were repeated except for using 2.00 g of 2-(3,7,11,15-tetramethyl-2-hexadecenyl-1,4-hydroquinone in place of 500 mg of 2-[3.7(R),11(R),15-tetramethyl-2-hexadecen-1-yl]-1,4-hydroquinone used in Example 8 to obtain 2.38 g of the title compound (10). Yield=98%.

$^1$H NMR (200 MHz, CDCl$_3$):
δ=0.8-2.0(36H,m), 2.28(3H,s), 2.30(3H,s),
3.22(2H,d), 5.20(1H,t), 6.9-7.0(3H,m).

IRν $^{max}$cm−1 (neat) =2950, 2930, 2870, 1770, 1500, 1370, 1210, 1180.

EXAMPLE 11

2-(3,7,11,15,19-Pentamethyl-2,6,10,14,18-eicosapentaenyl)-1,4-hydroquinone (Compound 11)

Phosphorus tribromide (35 ml;0.37 mole) was dropwise added to a solution of geranyllinalool (261 g;0.900 mole) in 500 ml of isopropyl ether with stirring and ice-cooling. The resulting solution was further stirred at that temperature for one hour and 15 ml methanol was dropwise added thereto in order to decompose excess phosphorus tribromide. The reaction solution was poured into water to cause phase separation (liquid/liquid), the organic phase was washed in order with water and saturated aqueous solution of sodium chloride and was dried over anhydrous sodium sulfate followed by evaporating it to dryness under a reduced pressure to recover 318 g (0.90 mole) of geranylgeranyl bromide. Then, this bromide was dissolved in 600 ml of isopropyl ether and a mixture of 28% methanolic sodium methylate solution (260 g;1.35 mole) and ethyl acetoacetate (176 g;1.35 mole) was dropwise added to the solution while stirring and ice-cooling. The temperature thereof was brought back to room temperature, was stirred overnight, was heated up to 40° C. followed by dropwise adding 740 ml of 10% (w/v) aqueous sodium hydroxide solution thereto while stirring and refluxing the solution under heating for additional 12 hours. The reaction solution was acidified by the addition of dilute hydrochloric acid and then separated into phases. The water phase was again extracted with isopropyl ether, the extract was combined with the organic phase previously obtained and the combined extract was washed with water and saturated aqueous solution of sodium chloride. The extract was dried over anhydrous magnesium sulfate and evaporated to dryness in vacuo to obtain 230 g (0.69 mole) of a crude product of ketone-form. Then, 271 g (0.97 mole) of ethyl diethyl phosphonoacetate was dropwise added to a solution of sodium methylate (54 g;1.0 mole) in toluene (350 ml) with ice-cooling and continuous stirring. After stirring at that temperature for additional 1.5 hours, the ketone-form previously prepared (230 g) was dropwise added thereto. The resultant solution was stirred at this temperature for 3 hours, then brought back to room temperature and further stirred overnight. This reaction solution was poured into 800 ml of water and was extracted with toluene and the organic phase was washed with water and then with saturated aqueous solution of sodium chloride. The extract was dried over anhydrous magnesium sulfate and the solvent was distilled off to obtain 290 g (0.72 mole) of a product in ester-form. The product was dissolved in 600 ml of toluene, 244 g (0.87 mole) of sodium bis (2-methoxyethoxy) aluminum hydride was dropwise added to the solution while ice-cooling and stirring, then it was brought back to room temperature and stirred overnight. 100 ml of ethyl acetate was dropwise added to the reaction solution at room temperature, then ice-cooled, and 120 ml of conc. hydrochloric acid was dropwise added thereto. This was extracted with toluene, the extract was washed with water and saturated aqueous solution of common salt, was dried over anhydrous magnesium sulfate, followed by distilling off the solvent and subjecting the resultant residue to a chromatography treatment using a column packed with silica gel. Thus, 116 g (0.325 mole) of 3,7,11,15,19-pentamethyl-2,6,10,14,18-eicosapentaen-1-ol from the fractions eluted through the column with hexane-toluene (1:1) in a 36% yield. Then the product in alcohol-form (3.6 g;10 mmole) obtained above was dropwise added to a dioxane solution of 1,4-hydroquinone (4.4 g;40 mmole) and boron trifluoride ethyl etherate (2.1 g;15 mmole) at 40° C. After stirring the solution at that temperature for additional one hour, the reaction solution was extracted with ether. The extract was washed in order with 5% (w/v) aqueous solution of sodium hydroxide, water and saturated aqueous solution of sodium chloride and dried over anhydrous magnesium sulfate. The solvent was distilled off and the resultant residue was chromatographed through a silica gel column to obtain 1.5 g (3.3 mmole) of 2-(3,7,11,15,19-pentamethyl-2,6,10,14,18-eicosapentaenyl)-1,4-hydroquinone from the fractions eluted through the silica gel column with an eluent, hexane ethyl acetate (3:1) in an yield of 33%. The overall yield starting from geranyllinalool was 12%.

$^1$H NMR (200 MHz, CDCl$_3$):
δ=1.5–2.3(36H,m), 3.29(2H,d,J=6.6 Hz),
4.64(s,1H), 4.83(1H,s), 5.0–5.2(4H,m),
5.29(1H,t), 6.5–6.7(3H,m).
IRv $^{max}$cm−1 (neat) =3390, 2970; 2925; 2850; 1510; 1460, 1380, 1195.

EXAMPLE 12

2-(3,7,11,15,19,23-Hexamethyl-2,6,10,14,18,22-tetracosahexaenyl)-1,4-hydroquinone (Compound 12)

The similar procedures as in Example 11 were repeated except for substituting 116 g (324 mmole) of 3,7,11,15,19-pentamethyl-2,6,10,14,18-eicosapentaen-1-ol for geranyllinalool in Example 11 to prepare 3,7,11,15,19,23-hexamethyl-2,6,10,14,18,22-tetracosahexaen-1-ol (54.7 g;128 mmole) in an yield of 40%. Then, the product in alcohol-form (3.00 g;7.04 mmole) was condensed with 3.10 g (28.2 mmole) of 1,4-hydroquinone in accordance with the method disclosed in Example 11 to obtain 0.95 g (1.8 mmole) of the title compound in a 26% yield. The overall yield thereof from 3,7,11,15,19-pentamethyl-2,6,10,14,18-eicosapentaen-1-ol (starting material) was 10%.

$^1$H NMR (200 MHz, CDCl$_3$):
δ=1.5–2.2(43H,m), 3.29(2H,d,J=7.1 Hz),
4.87(1H,s), 4.88(1H,s), 5.0–5.2(5H,m),
5.29(1H,t), 6.5–6.7(3H,m).
IRv $^{max}$cm−1 (neat) =3390, 2970, 2925, 2850 1505; 1455, 1380, 1200.

EXAMPLE 13

2-(3,7,11,15,19,23,27-Heptamethyl-2,6,10,14,18,22,26-octacosaheptaenyl)-1,4-hydroquinone (Compound 13)

The same procedures as in Example 11 were repeated except for substituting 3,7,11,15,19,23-hexamethyl-2,6,10,14,18,22-tetracosahexaen-1-ol (41.5 g;97.4 mmole) for geranyllinalool used in Example 11 to obtain 19.8 g (40.1 mmole) of 3,7,11,15,19,23,27-heptamethyl-2,6,10,14,18,22,26-octacosaheptaen-1-ol in an yield of 40%. Then, the product in alcohol-form (4.9 g;9.9 mmole) was condensed with 4.4 g (40 mmole) of 1,4-hydroquinone according in the same manner as in Example 11 to form 1.81 g (3.09 mmole) of the title compound in a 31% yield. The overall yield from the starting material was 12%.

$^1$H NMR (200 MHz, CDCl$_3$):
δ=1.5–2.3(50H,m), 3.30(2H,d,J=7.3 Hz),
4.75(1H,s), 4.87(1H,s), 5.0–5.2(6H,m),
5.29(1H,t), 6.5–6.7(3H,m).
IRv $^{max}$cm−1 (neat) =3400, 2970, 2925, 2850, 1505, 1455, 1380, 1195.

EXAMPLE 14

2-Solanesyl-1,4-hydroquinone (Compound 14)

A solution of solanesol (14.1 g;25.0 mmole) in dioxane (25 ml) was dropwise added to a solution of 1,4-hydroquinone (5.51 g;50.0 mmole) and boron trifluoride ethyl etherate (2.84 g;20.0 mmole) in dioxane (50 ml) at 40° C. over one hour. The reaction solution was stirred at that temperature for one hour, was poured into water (500 ml) and was extracted twice with diethyl ether (300 ml). The extract was washed once with 5% aqueous sodium hydroxide solution (500 ml), once with water (500 ml) and once with saturated aqueous sodium chloride solution (500 ml) followed by drying over anhydrous magnesium sulfate, distilling off the solvent and recrystallizing the residue obtained from hexane (primary crystals=1.79 g; secondary crystals=1.87 g). The mother liquor from which the secondary crystals had been recovered was chromatographed through a silica gel column to recover 1.04 g of tertiary crystals from the fractions eluted with hexane-ethyl acetate (5:1). The overall yield was 29% (4.70 g). M.P.=50.0°–53.5° C. (for the primary crystals); 52.0°–54.0° C. (for the secondary crystals) and 50.0°–54.0° C. (for the tertiary crystals).

$^1$H NMR (200 MHz, CDCl$_3$):
δ=1.6–2.2(62H,m), 3.30(2H,d,J=7.3 Hz),
4.5–5.0(2H,bs), 5.1–5.4(9H,m), 6.5–6.7(3H,m).
IRv $^{max}$cm−1 (neat) =3350, 2970; 2950; 2950; 2920; 2850, 1500, 1450, 1390, 1190, 880, 800.

EXAMPLE 15

2,6-Di-tert-butyl-4-(3,7,11,15-tetramethyl-2-hexadecenyl)-phenol (Compound 15)

A solution of 3,7,11,15-tetramethyl-2-hexadecen-1-ol (2.97 g;10.0 mmole) in dioxane (8 ml) was dropwise added to a solution of 2,6-di-tert-butyl phenol (4.13 g;200 mmole) and boron trifluoride ethyl etherate (0.86 g;6.0 mmole) in dioxane (20 ml) at 40° C. over one hour. After stirring the resultant solution at that temperature for 2.5 hours, the reaction solution was poured into water (30 ml) and was then extracted once with ethyl acetate (20 ml). The extract was successively washed with 30 ml of 5% (w/v) aqueous sodium hydroxide solution containing 3% (w/v) sodium hydrosulfite (once), 30 ml of water (twice) and then 30 ml of saturated aqueous sodium chloride (once) and was dried over anhydrous magnesium sulfate. Then, the solvent and the unreacted 2,6-di-tert-butyl-phenol were distilled off and the resultant residue was subjected to silica gel column chromatography to obtain 440 mg (0.91 mmole) of 2,6-di-tert-butyl-4-(3,7,11,15,tetramethyl-2-hexadecenyl)-phenol from the fractions eluted through the column with hexane-ethyl acetate (50:1). Yield=9.1%.

$^1$H NMR (200 MHz, CDCl$_3$):
δ=0.8–1.7(52H,m), 2.01(2H,t), 3,29(2H,d), 5.03(1H,s), 5.34(1H,t), 6.98(2H,s).
IRν $^{max}$cm$-1$ (neat) =3650, 2960; 2930; 2870; 1460, 1440, 1240, 1160.

EXAMPLE 16

3-(3,7,11,15-Tetramethyl-2-hexadecenyl)-1,2-benzenediol (Compound 16)

A solution of 3,7,11,15-tetramethyl-2-hexadecen-1-ol (2.97 g;10.0 mmole) in dioxane (7 ml) was dropwise added to a solution of 1,2-benzenediol (2.20 g;20.0 mmole) and boron trifluoride ethyl etherate (850 mg;6.0 mmole) in dioxane (20 ml) at 40° C. over 30 minutes. After stirring the resulting reaction solution at that temperature for 1.5 hours, the solution was poured into water (30 ml) and was extracted twice with ethyl acetate (20 ml). The extract was washed with 30 ml of 5% (w/v) aqueous sodium hydroxide solution containing 1% sodium hydrosulfite (one time), 30 ml of water (two times) and 30 ml of saturated aqueous sodium chloride solution (one time) and was dried over anhydrous magnesium sulfate. Then, the solvent was distilled off and the resultant residue was chromatographed through a silica gel column to obtain 250 mg (0.64 mmole) of 3-(3,7,11,15-tetramethyl-2-hexadecenl)-1,2-benzenediol from the fractions eluted with hexane-ethyl acetate (5:1). Yield=6.4%.

$^1$H NMR (200 MHz, CDCl$_3$):
δ=0.8–1.7(31H,m), 1.78(3H,s), 2.03(2H,t), 3.37(2H,d), 5.33(1H,t), 5.37(1H,s), 5.42(1H,s)6.6–6.8(3H,m).
IRν $^{max}$cm$-1$ (neat) =3450, 2950, 2930, 1480 1380, 1370, 1280, 1180.

EXAMPLE 17

4-(3,7,11,15-Tetramethyl-2-hexadecenyl)-1,2-benzenediol (Compound 17)

In the synthetic method as described in Example 16, the title compound (760 mg;2.0 mmole) was recovered from another fraction obtained during the silica gel column chromatography. Yield=20%.

$^1$H NMR (200 MHz, CDCl$_3$):
δ=0.8–1.6(31H,m), 1.68(3H,s), 1.99(2H,t), 3.24(2H,d,J=7.8 Hz), 5.15(2H,bs), 5.28(1H,t), 6.62(1H,d,J=8.3 Hz), 6.69(1H,s), 6.77(1H,d,J=8.3 Hz).
IRν $_{max}$cm$-1$ (neat) =3380, 2950; 2930; 2870; 1520; 1460, 1380, 1280, 1110.

EXAMPLE 18

4-(3,7,11,15-Tetramethyl-2-hexadecenyl)-1,2-dimethoxybenzene (Compound 18)

There was dropwise added a solution of 3,7,11,15-tetramethyl-2-hexadecen-1-ol (2.97 g;10.0 mmole) in dioxane (8 ml) to a solution of 1,2-dimethoxybenzene (2.76 g;20.0 mmole) and boron trifluoride ethyl etherate (0.86 g;6.0 mmole) in dioxane (20 ml) at 40° C. over 30 minutes. The resulting reaction solution was stirred at that temperature for 2 hours, then was poured into water (30 ml) and was extracted with ethyl acetate (30 ml). The extract was washed twice with water (30 ml) and once with 30 ml of saturated aqueous sodium chloride solution and was dried over anhydrous magnesium sulfate. Then, the solvent was distilled off and the resultant residue was chromatographed using a silica gel column to recover 1.79 g (4.30 mmole) of 4-(3,7,11,15-tetramethyl-2-hexadecenyl)-1,2-dimethoxybenzene from the fractions eluted with hexane-ethyl acetate (10:1). Yield=21%.

$^1$H NMR (200 MHz, CDCl$_3$):
δ=0.8–1.6(31H,m), 1.70(3H,s), 2.01(2H,t,J=7.2 Hz), 3.30(2H,d,J=7.1 Hz), 3.85(3H,s), 3.86(3H,s), 5.32(1H,bt), 6.72(2H,d), 6.77(1H,s).
IRν $_{max}$cm$-1$ (neat) =2950, 2930, 2870, 1520, 1470, 1260, 1240, 1160 1140, 1040.

EXAMPLE 19

4-(3,7,11,15-Tetramethyl-2-hexadecenyl)-1,2,3-benzenetriol (Compound 19)

3,7,11,15-Tetramethyl-2-hexadecen-1-ol (89.0 g;300 mmole) was dropwise added to 75.7 g (600 mmole) of 1,2,3-benzenetriol and 25.5 g (180 mmole) of boron trifluoride ethyl etherate in 300 ml of dioxane at room temperature over 2 hours. The resultant reaction solution was stirred at that temperature overnight and was poured into 500 ml of 5% (w/v) aqueous sodium hydroxide solution containing 3% (w/v) sodium hydrosulfite while ice-cooling and then 300 ml of isopropyl ether was added to cause liquid/liquid phase separation. The organic phase was washed with 500 ml of 5% (w/v) aqueous sodium hydroxide solution containing 3% (w/v) sodium hydrosulfite (once), 500 ml of 5% HCl aqueous solution (twice), 500 ml of water (twice) and 500 ml of saturated aqueous sodium chloride solution (once) and was dried over anhydrous magnesium sulfate. The solvent was distilled off therefrom and the residue obtained was treated by silica gel column chromatography. Thus, 22.5 g (55.6 mmole) of 4-(3,7,11,15-tetramethyl-2-hexadecenyl)-1,2,3-benzenetriol was recovered from the fractions eluted with hexane-ethyl acetate (3:1). Yield=19%.

$^1$H NMR (200 MHz, CDCl$_3$) : δ=0.8–1.6(31H,m), 1.77(3H,s), 2.02 (2H,t,J=5.4 Hz), 3.31(2H,d,J=8.6 Hz), 5.06(1H,bs), 5.2–5.3(2H,m), 5.42 (1H,bs), 6.44(1H,d,J=8.6 Hz), 6.54 (1H,d,J=8.3 Hz).
IRν$_{max}$$^{cm-1}$ (neat)=3430, 2950, 2930, 2860 1630, 1510, 1460, 1380, 1300, 1030.

EXAMPLE 20

2-Methyl-2-(4-methyl-3-pentenyl)-6-chromenol (Compound 20)

Geraniol (23.1 g; 150 mmole) was dropwise added to 33.0 g (300 mmole) of 1,4-hydroquinone and 17.0 g (120 mmole) of boron trifluoride ethyl etherate in 300 ml of dioxane at 50° C. over one hour. After stirring the resultant solution at that temperature for 2 hours, the reaction solution was poured into 500 ml of water and was extracted twice with diethyl ether (200 ml). The extract was washed successively with 700 ml of aqueous sodium hydroxide solution (once), 700 ml of water (twice) and 700 ml of saturated aqueous sodium chloride solution (once) and then dried over anhydrous magnesium sulfate. Then the solvent was removed by distillation and the resulting residue was subjected to silica gel column chromatography. The fractions eluted through the column with hexane-ethyl acetate (3:1) was evaporated to dryness in vacuo to thus obtain 6.8 g of waxy substance. This was dissolved in 30 ml of diethyl ether, 33 g (140 mmole) of lead dioxide was added to the solution and the solution was stirred at room temperature for two days. After filtering off lead dioxide, the filtrate was concentrated and the concentrate was chromatographed through a silica gel column. Thus, 1.46 g (5.98 mmole) of 2-geranyl-1,4-benzoquinone was obtained, in an yield of 3.8%, from the fractions eluted with hexane-ethyl acetate (5:1). Then, this compound (1.10 g; 4.50 mmole) was dissolved in 10 ml of pyridine and the solution was heated under reflux for 6 hours. The reaction solution was poured into 75 ml of ice-water and was extracted three times with diethyl ether (25 ml). The extract was washed with 100 ml of water (twice) and 100 ml of saturated aqueous sodium chloride solution (twice) and then dried over anhydrous magnesium sulfate. The solvent was distilled off and the resulting residue was chromatographed through a silica gel column. Thus, 490 mg (2.0 mmole) of 2-methyl-2-(4-methyl-3-pentenyl)-6-chromenol was recovered. Yield=45%. The overall yield from geraniol was 1.7%.

$^1$H NMR (200 MHz, CDCl$_3$): δ=1.36(3H,s), 1.4–2.1(10H,m), 4.59 (1H,s), 5.08(1H,bt), 5.59(1H,d,J=9.8 Hz), 6.27(1H,d,J=9.8 Hz), 6.4–6.7(3H,m).

IRv$_{max}$$^{cm-1}$ (neat)=3400, 2970, 2930, 1490 1460, 1280, 1230, 1200 920, 720.

EXAMPLE 21

2-Methyl-2-(4,8-dimethyl-3,7-nonadienyl)-6-chromenol (Compound 21)

Farnesol (33.4 g; 150 mmole) was dropwise added to a solution of 1,4-hydroquinone (33.0 g; 300 mmole) and boron trifluoride ethyl etherate (17.0 g; 120 mmole) in 300 ml of dioxane at 50° C. over two hours. After stirring the resultant solution at that temperature for two hours, the reaction solution was poured into 500 ml of water and was extracted twice with diethyl ether (500 ml). The extract was washed once with 500 ml of 5% (w/v) aqueous sodium hydroxide solution, twice with water (500 ml) and then once with saturated aqueous solution of sodium chloride (500 ml) and then dried over anhydrous magnesium sulfate. Then, the solvent was distilled off and the resultant residue was chromatographed with a silica gel column. The fractious eluted with hexane-ethyl acetate (3:1) was evaporated to dryness to thereby obtain 6.63 g of waxy substance. This was dissolved in 40 ml of diethylether, then 24.5 g (103 mmole) of lead dioxide was added thereto and the solution was stirred at room temperature for two days. After removing lead dioxide by filtration, the filtrate was concentrated and the concentrate was chomatographed through a column packed with silica gel to obtain 1.1 g (3.5 mmole) of 2-farnesyl-1, 4-benzoquinone from the fractions eluted through the column with hexane-ethyl acetate (10:1) in an yield of 2.3%. Then, this compound (1.08 g; 3.46 mmole) was dissolved in 5 ml of pyridine and was heated under reflux for 2.5 hours. The reaction solution was poured into 50 ml of ice-water and was extracted twice with diethyl ether (50 ml). The extract was washed twice with water (50 ml) and then once with saturated aqueous sodium chloride solution (50 ml) followed by drying it over anhydrous magnesium sulfate, distilling off the solvent and subjecting the resultant residue to silica gel column chromatography. Thus, 470 mg (1.5 mmole) of 2-methyl-2-(4,8-dimethyl-3,7-nonadienyl)-6-chromenol was recovered from the fractions eluted with hexane-ethyl acetate (5:1) in an yield of 44% which corresponded to the overall yield, from farnesol, of 1.0%.

$^1$H NMR(200 MHz, CDCl$_3$): δ=1.3~ −0.2(20H,m), 4.60(1H,s), 5.0–5.2(2H,m), 5.59(1H,dd,J=10.0H$_z$, 2.7 H$_z$) 6.27(1H,d), 6.4~6.7(3H,m).

IRv$_{max}$$^{cm-1}$ (neat)=3400, 2970, 1490, 1460, 1380, 1220.

EXAMPLE 22

2-Methyl-2-(4,8,12-trimethyl-3,7,11-tridecatrienyl)-6-chromenol (Compound 22)

Geranyllinalool (29.0 g; 100 mmole) was dropwise added to a solution of 1,4-hydroquinone (22.0 g; 200 mmole) and boron trifluoride ethyl etherate (11.4 g; 80.0 mmole) in dioxane (200 ml) at 50° C. over one hour. After stirring the solution at that temperature for one hour, the reaction solution was poured into 500 ml of water and then extracted twice with diethyl ether (400 ml). The extract was washed with 400 ml of 5% (w/v) aqueous sodium hydroxide solution (once), 400 ml of water (twice) and 400 ml of saturated aqueous sodium chloride solution (once) and was dried over anhydrous magnesium sulfate. Then, the solvent was distilled off and the residue obtained was subjected to silica gel column chromatography. The fractions eluted with hexane-ethyl acetate (3:1) was evaporated to dryness to thus obtain 11.6 g of waxy substance. The substance was then dissolved in 55 ml of diethyl ether, 35.9 g (150 mmole) of lead dioxide was added thereto and the solution was stirred at room temperature for two days. After removing lead dioxide by filtration, the filtrate was concentrated and the concentrate was chromatographed through a silica gel column to thereby obtain 2.0 g of 2-geranylgeranyl-1,4-benzoquinone from the fraction eluted with hexane-ethyl acetate (10:1) in a 5.4% yield. Then, this compound (1.06 g: 2.79 mmole) was dissolved in 6 ml of pyridine and the solution was refluxed for two hours. The reaction solution was poured into 50 ml of ice-water and was extracted twice with diethyl ether (50 ml). The extract was washed twice with water (100 ml) and once with 100 ml of saturated aqueous sodium chloride solution and then was dried over anhydrous magnesium sulfate, followed by removing the solvent through distillation and subjecting residue obtained to silica gel column chromatography to thereby recover 370 mg (0.97 mmole) of 2-methyl-2-(4,8,12-trimethyl-3,7,11-tridecatrienyl)-6-chromenol from the fractions eluted with hexane-ethyl acetate (5:1) in an yield of 35% which corresponded to the overall yield, from geranyllinalool, of 1.9%.

$^1$H NMR (200 MHz, CDCl$_3$): δ=1.3–2.2(27H,m), 4.50(1H,s), 5.0–5.2(3H,m), 5.60(1H,d,J=9.8H$_z$), 6.27(1H,d,J=10H$_z$), 6.4–6.7(3H,m).

IRv$_{max}^{cm-1}$ (neat)=3400, 2970, 2920, 2850, 1490, 1460, 1390, 1210.

EXAMPLE 23

2-(3,7,11,15-Tetramethyl-2-hexadecenyl)-1,4-benzoquinone (Compound 23)

To a solution of 1,4-hydroquinone (11.0 g; 100 mmole) and boron trifluoride ethyl etherate (5.68 g; 40.0 mmole) in 100 ml of dioxane there was dropwise added a solution of 3,7,11,15-tetramethyl-2-hexadecen-1-ol (14.8 g; 50.0 mmole) in 30 ml of dioxane at 40° C. over one hour. After stirring the solution at that temperature for 30 minutes, the reaction solution was poured into 500 ml of water and was extracted twice with diethyl ether (500 ml). The extract was washed with 700 ml of 5% (w/v) aqueous sodium hydroxide solution (once), 700 ml of water (twice) and 700 ml of saturated aqueous sodium chloride (once) followed by drying it over anhydrous magnesium sulfate, removing the solvent by distillation and subjecting the residue obtained to silica gel column chromatography to thereby recover 8.86 g (22.8 mmole) of 2-(3,7,11,15-tetramethyl-2-hexadecenyl)-1,4-hydroquinone from the fraction eluted with hexane-ethyl acetate (3:1). Yield=46%. Then, 4.00 g (10.3 mmole) of the compound was dissolved in 12 ml of diethyl ether and the solution was stirred at room temperature for two days after the addition of lead dioxide (12.3 g; 51.5 mmole). After removing lead dioxide by filtration, the mother liquor was concentrated and the concentrate was chromatographed through a silica gel column. Thus, 1.71 g (4.42 mmole) of 2-C (3,7,11,15-tetramethyl-2-hexadecenyl)-1,4-benzoquinone was recovered from the fractions eluted with hexane-ethyl acetate (10:1) in an yield of 43% which corresponded to the overall yield, from the starting material, of 20%.

$^1$H NMR (200 MHz, CDCl$_3$): δ=0.8–2.1(33H,m), 3.13(2H,d,J=7.1H$_z$), 5.14(1H,bt), 6.5–6.8 (3H,m).

IRv$_{max}^{cm-1}$ (neat)=2960, 2930, 2870, 1660, 1600, 1470, 1300, 900.

EXAMPLE 24

2-[3,7(R),11(R),15-Tetramethyl-2-hexadecenyl]-1,4-benzoquinone (Compound 24)

A solution of 3,7(R),11(R),15-tetramethyl-2-hexadecen-1-ol (14.8 g: 50.0 mmole) in dioxane (30 ml) was dropwise added to a solution of 1,4-hydroquinone (11.0 g; 100 mmole) and boron trifluoride ethyl etherate (5.7 g; 40 mmole) in dioxane (100 ml) at 40° C. over one hour. After stirring the resultant mixed solution at that temperature for 30 minutes, the reaction solution was poured into 500 ml of water and was extracted twice with diethyl ether (500 ml). The extract was washed with 700 ml of 5% (w/v) aqueous sodium hydroxide solution (once), 700 ml of water (twice) and 700 ml of saturated aqueous sodium chloride solution (once) followed by drying it over anhydrous magnesium sulfate, distilling off the solvent and subjecting the resulting residue to silica gel column chromatography to thereby obtain 10.9 g (28.0 mmole) of 2-[3,7(R),11(R),15-tetramethyl-2-hexadecenyl]-1,4-hydroquinone from the fractions eluted with hexane-ethyl acetate (3:1) in an yield of 56%. Then, 3.00 g (7.72 mmole) of the compound was dissolved in diethyl ether (30 ml) and was stirred at room temperature for 3.5 days after the addition of lead dioxide (9.23 g;38.6 mmole). After removing lead dioxide by filtration, the mother liquor was concentrated and the resultant residue was chromatographed through a silica gel column. Thus, 510 mg (1.31 mmole) of 2-[3,7(R),11(R),15-tetramethyl-2-hexadecenyl]-1,4-benzoquinone was obtained from the fractions eluted with hexane-ethyl acetate (10:1) Yield=17%. The overall yield thereof, from d-phytol, was 9.5%.

$^1$H NMR (200 MHz, CDCl$_z$): δ=0.8–2.1(36H,m), 3.13 (2H,d,J=7.1H$_z$), 5.14 (1H,bt), 6.5–6.8 (3H,m).

IRv$_{max}^{cm-1}$ (neat)=2950, 2920, 2870, 1660, 1600, 1480, 1300, 900.

EXAMPLE 25

4-(3,7,11,15-Tetramethyl-2-hexadecenyl)-1,3-diacetoxybenzene (Compound 25)

In 5 ml of pyridine, there was dissolved 780 mg (2.0 mmole) of 4-(3,7,11,15-tetramethyl-2-hexadecenyl)-1,3-benzenediol and 450 mg (4.4 mmole) of acetic anhydride was added thereto with ice-cooling. The temperature of the solution was brought back to room temperature followed by stirring overnight, distilling off the solvent and subjecting the resultant residue to silica gel column chromatography. Thus, the title compound (610 mg) was recovered from the fractions eluted with hexane-ethyl acetate (10:1). Yield =64%.

$^1$H NMR (200 MHz, CDCl$_3$) δ=0.84(6H,d,J=5.9H$_z$), 0.86(6H,d,J=6.6H$_z$), 1.0–1.6(19H,m), 1.67(3H,s), 1.99(2H,t,J=7.2H$_z$), 2.27(3H,s), 2.29(3H,s), 3.22(2H,d,J=6.8H$_z$), 5.20(1H,bt), 6.85(1H,d,J=2.2H$_z$), 6.92(1H,dd,J=8.4H$_z$/2.3H$_z$), 7.24(1H,s).

IRv$_{max}^{cm-1}$ (neat)=2950, 2930, 2860, 1770, 1500, 1370, 1200.

EXAMPLE 26

4-(3,7,11,15-Tetramethyl-2-hexadecenyl)-1,3-benzenediol (Compound 26)

3,7,11,15-Tetramethyl-2-hexadecen-1-ol(14.8 g; 50 mmole) in 15 ml of dioxane was dropwise added to 11.0 g (100 mmole) of 1,3-benzenediol and 4.3 g (30 mmole) of boron trifluoride ethyl etherate in 30 ml of diozane at room temperature over one hour. After stirring the reaction solution at that temperature overnight, the solution was poured into 75 ml of water and was extracted with isopropyl ether (100 ml). The extract was washed with 200 ml of water (3 times) and 200 ml of saturated aqueous solution of sodium chloride (3 times) followed by drying it over anhydrous magnesium sulfate, distilling off the solvent and subjecting the resulting residue to silica gel column chromatography to thereby obtain 2.80 g of the title compound from the fractions eluted with hexane-ethyl acetate (3:1). Yield=14%.

$^1$H NMR (200 MHz, CDCl$_3$) δ=0.84(6H,d,J=6.1H$_z$), 0.86(6H,d,J=6.6H$_z$), 1.0–1.7(19H,m), 1.76(3H,S), 2.02(2H,bt), 3.29(2H,d,J=7.3H$_z$), 4.91(1H,s), 5.26(1H,s), 5.2–5.4(1H,m), 6.3–6.5(2H,m), 6.93(1H, d, J=8.5H$_z$).

IRv$_{max}^{cm-1}$ (neat)=3380, 2950, 2930, 2870, 1620, 1610, 1520, 1460, 1160, 980.

EXAMPLE 27

2-(3,7,11,15-Tetramethyl-2-hexadecenyl)-1,3,5-triacetoxybenzene (Compound 27)

2-(3,7,11,15-Tetramethyl-2-hexadecenyl)-1,3,5-benzenetriol (1.00 g;2.47 mmole) was dissolved in 10 ml of pyridine and 833 mg (8.16 mmole) of acetic anhydride was added thereto with ice-cooling, followed by bringing it back to room temperature, stirring for 4 hours, removing the solvent by distillation and subjecting the resulting residue to silica gel column chromatography to thereby recover 0.77 g of the title compound from the fractions eluted with hexane-ethyl acetate (5:1). Yield=59%.

$^1$H NMR (200MH$_z$, CDCl$_3$) δ=0.8–1.6(31H,m), 1.69(3H,S), 1.91(2H,bt), 2.25(3H,S), 2.27(6H,S), 3.16(2H,d,J=7.1H$_z$), 4.99(1H,bt), 6.83(2H,S).

IRν$_{max}^{cm-1}$ (neat)=2950, 2930, 2860, 1780, 1430, 1370, 1200, 1120, 1040, 1020.

EXAMPLE 28

2-(3,7,11,15-Tetramethyl-2-hexadecenyl)-1,3,5-benzenetriol (Compound 28)

3,7,11,15-Tetramethyl-2-hexadecen-1-ol (14.8 g; 50 mmole) in dioxane (10 ml) was dropwise added to 16.2 g (100 mmole) of 1,3,5-benzenetriol·dihydrate and 4.3 g (30 mmole) of boron trifluoride ethyl etherate in dioxane (35 ml) at room temperature over one hour. After stirring the resulting reaction solution at that temperature overnight, it was further stirred at 50° C. for additional 3 hours, then poured into 150 ml of water and was extracted with 150 ml of isopropyl ether. The extract was washed twice with 150 ml of water and once with 150 ml of saturated aqueous solution of sodium chloride followed by drying it over anhydrous magnesium sulfate, distilling off the solvent and subjecting the resultant residue to silica gel column chromatography. Thus, 6.4 g of the title compound was recovered from the fractions eluted with hexane-ethyl acetate (2:1). Yield=32%.

$^1$H NMR (200MH$_z$, CDCl$_3$) δ=0.8–1.6(31H,m), 1.79(3H,S), 2.00(2H,bt), 3.33(2H,d,J=6.4H$_z$), 5.28(1H,bt), 5.4–5.5(3H,m), 5.94(2H,S).

IRν$_{max}^{cm-1}$ (neat)=3400, 2960, 2930, 2870, 1630, 1470, 1380, 1270, 1150, 1040, 1010.

EXAMPLE 29

4-(3,7,11,15-Tetramethyl-2-hexadecenyl)-1,2,3-triacetoxybenzene (Compound 29)

2-(3,7,11,15-Tetramethyl-2-hexadecenyl)-1,2,3-benzenetriol (500 mg;1.24 mmole) was dissolved in 5 ml of pyridine and 417 mg (4.08 mmole) of acetic anhydride was added thereto while ice-cooling, followed by bringing it back to room temperature, stirring for two hours, distilling off the solvent and subjecting the resulting residue to silica gel column chromatography to thereby recover 370 mg the title compound from the fractions eluted with hexane-ethyl acetate (5:1). Yield=56%.

$^1$H NMR (200MH$_z$, CDCl$_3$) δ=0.84(6H,d,J=6.1H$_z$), 0.86(6H,d,J=6.6H$_z$), 0.9–1.6(19H,m), 1.65(3H,S), 1.99(2H,bt), 2.25(3H,S), 2.27(3H,S), 2.29(3H,S), 3.23(2H,d,J=7.3H$_z$), 5.21(1H,bt), 7.05(1H,d,J=8.8HZ$_z$), 7.12(1H,d,J=8.5H$_z$).

IRν$_{max}^{cm-1}$ (neat)=2950, 2930, 2870, 1780, 1500, 1460, 1370, 1280, 1210, 1190, 1170, 1040, 1020.

EXAMPLE 30

2-Methyl-2-(4,8,12-trimethyltridecyl)-7-chromanol (Compound 30)

A solution of 4-(3,7,11,15-tetramethyl-2-hexadecenyl)-1,3-benzenediol (870 mg; 2.24 mmole) and conc. hydrochloric acid (2.0 ml) in methanol (15 ml) was heated under reflux for 4 hours, then the reaction solution was poured into 70 ml of water and was extracted twice with isopropyl ether (50 ml). The extract was washed with 100 ml of water (twice) and 100 ml of saturated aqueous solution of sodium chloride (once), followed by drying it over anhydrous magnesium sulfate, distilling off the solvent and subjecting the resultant residue to silica gel column chromatography to thus obtain 610 mg of the title compound from the fractions eluted with hexane-ethyl acetate (10:1). Yield=70%.

$^1$H NMR (200MH$_z$,CDCl$_3$) δ=0.9–1.9(38H,m), 2.66(2H,t,J=6.8H$_z$), 4.73(1H,bs), 6.27(1H,d,J=2.7H$_z$), 6.33(1H,dd,J=8.1H$_z$/2.4H$_z$), 6.89(1H,d,J=8.1H$_z$).

IRν$_{max}^{cm-1}$ (neat)=3400, 2950, 2930, 2870, 1630, 1600, 1510, 1460, 1380, 1150, 1010, 990.

EXAMPLE 31

2-Methyl-2-(4,8,12-trimethyltridecyl)-7,8-dichromanol (Compound 31)

A solution of 4-(3,7,11,15-tetramethyl-2-hexadecenyl)-1,2,3-benzenetriol (650 mg; 1.61 mmole) and conc. hydrochloric acid (1.3 ml) in methanol (6.5 ml) was heated under reflux for 5 hours, the reaction solution was poured into 50 ml of water and was extracted with isopropyl ether (50 ml). The extract was washed twice with 50 ml of water and once with 50 ml of saturated aqueous solution of sodium chloride, followed by drying it over anhydrous magnesium sulfate, removing the solvent by distillation and subjecting the resulting residue to silica gel column chromatography to thereby recover 430 mg of the title compound from the fractions eluted with hexane-ethyl acetate (2:1). Yield=66%.

$^1$H NMR (200MH$_z$, CDCl$_3$) δ=0.8–1.9(38H,m), 2.68(2H,t,J=6.8H$_z$), 5.14(1H,S), 5.31(1H,S), 6.45(1H,d,J=8.5H$_z$), 6.51(1H,d,J=8.5H$_z$).

IRν$_{max}^{cm-1}$ (neat)=3450, 2950, 2930, 2870, 1630, 1520, 1470, 1380, 1350, 1270, 1200, 1150.

EXAMPLE 32

2-Methyl-2-(4,8,12-trimethyltridecyl)-5,7-dichromanol (Compound 32)

A solution of 2-(3,7,11,15-tetramethyl-2-hexadecenyl)-1,3,5-benzenetriol (1.00 g; 2.47 mmole) and conc. hydrochloric acid (2.0 ml) in methanol (10 ml) was heated under reflux for 5 hours, and the reaction solution was poured into 100 ml of water and was extracted twice with isopropyl ether (100 ml). The extract was washed twice with 150 ml of water and once with 150 ml of saturated aqueous solution of sodium chloride, followed by drying it over anhydrous magnesium sulfate, distilling off the solvent and subjecting the resultant residue to silica gel column chromatography to thereby recover 0.46 g of the title compound from the fractions eluted with hexane-ethyl acetate (2:1). Yield=46%.

$^1$H NMR (200MH$_z$, CDCl$_3$) δ=0.8–1.9(38H,m), 2.54(2H,t,J=6.8H$_z$), 4.96(2H,bs), 5.92 (2H,S).

IRν$_{max}^{cm-1}$ (neat)=3400, 2950, 2930, 2870, 1640, 1610, 1510, 1470, 1380, 1150, 1080, 1060, 1020.

EXAMPLE 33

2-Methyl-2-(4,8,12-trimethyltridecyl)-8-chromanol (Compound 33)

3-(3,7,11,15-Tetramethyl-2-hexadecenyl)-1,2-benzenediol (1.00 g; 2.57 mmole) and conc. hydrochloric acid (2.0 ml) in 10 ml of methanol were heated under reflux for 4 hours, then the reaction solution was poured into 100 ml of water and was extracted twice with 50 ml of isopropyl ether. The extract was washed twice with 100 ml of water and once with 100 ml of saturated aqueous solution of sodium chloride, followed by drying it over anhydrous magnesium sulfate, distilling off the solvent and subjecting the resulting residue to silica gel column chromatography. Thus, 790 mg of the title compound was recovered from the fractions eluted through the column with hexane-ethyl acetate (30:1). Yield=79%.

$^1$H NMR (200MHz, CDCl$_3$) δ=0.9-1.9(38H,m), 2.74(2H,t,J=6.8H$_z$), 5.55(1H,S), 6.5-6.8 (3H,m).

IRν$_{max}$$^{cm-1}$ (neat)=3550, 2950, 2930, 2870, 1600, 1480, 1380, 1370, 1250, 1240, 1220, 1190, 770.

EXAMPLE 34

3-(3,7,11,15-Tetramethyl-2-hexadecenyl)-1,2-diacetoxybenzene (Compound 34)

3-(3,7,11,15-Tetramethyl-2-hexadecenyl)-1,2-benzenediol (0.90 g; 2.3 mmole) was dissolved in 3 ml of pyridine, 470 mg (4.6 mmole) of acetic anhydride was added thereto with ice-cooling, followed by bringing its temperature back to room temperature, stirring for 4 hours, distilling off the solvent and subjecting the resultant residue to silica gel column chromatography to thereby recover 0.87 g of the title compound from the fractions eluted with hexane-ethyl acetate (10;1). Yield=80%.

$^1$H NMR (200MHz, CDCl$_3$) δ=0.8-1.6(31H,m), 1.67(3H,S), 1.99(2H,t,J=7.3H$_z$), 2.28(3H,S), 2.30(3H,S), 3.25(2H,d,J=7.1H$_z$), 5.22(1H,t), 7.0-7.25(3H,m).

IRν$_{max}$$^{cm-1}$ (neat)=2950, 2920, 2850, 1770, 1460, 1370, 1260, 1210, 1160, 1100.

EXAMPLE 35

4-(3,7,11,15-Tetramethyl-2-hexadecenyl)-1,2-diacetoxybenzene (Compound 35)

4-(3,7,11,15-Tetramethyl-2-hexadecenyl)-1,2-benzenediol (1.00 g; 2.57 mmole) was dissolved in 5 ml of pyridine and 578 mg (5.66 mmole) of acetic anhydride was added thereto while ice-cooling followed by bringing its temperature back to room temperature, stirring the solution for 2.5 hour, removing the solvent thereof by distillation and subjecting the resultant residue to silica gel column chromatography to thereby recover 1.10 g of the title compound from the fractions eluted with hexaneethyl acetate (10:1). Yield 91%.

$^1$H NMR (200MHz,CDCl$_3$) δ=0.8-1.6(31H,m), 1.67(3H,s), 2.01(2H,t), 2.275(3H,s), 2.279(3H,s), 3.35(2H,d,J=7.1Hz), 5.30(1H,bt), 6.98(1H,s), 7.06(2H,s).

IRν$_{max}$$^{cm-1}$ (neat)=2950, 2920, 2850, 1780, 1500, 1370, 1260, 1210, 1180, 1100.

EXAMPLE 36

2-(3,7,11,15-Tetramethylhaxedecyl)-1,4-hydroquinone (Compound 36)

2-(3,7,11,15-Tetramethyl-2-hexadecenyl)-1,4-hydroquinone (1.96 g; 5.04 mmole) was dissolved in ethanol (10 ml), a suspension of Raney nickel W4 in ethanol (15 ml) was added thereto and then the mixture was reciprocatively shaken at 70° to 85° C. and a hydrogen pressure of 70 to 80 atm. for 2 days. After removing Raney's nickel by filtration, the filtrate was concentrated and the concentrate was chromatographed through a silica gel column. Thus, 1.27 g of the title compound was recovered from the fractions eluted with hexane-ethyl acetate (5:1). Yield=91%.

$^1$H NMR (200MHz,CDCl$_3$) δ=0.84(6H,d,J=6.3H.z), 0.86(6H,J=6.6Hz), 0.94(3H, J=6.1Hz), 1.0-1.8(24Hz,m), 2.5-2.6(2H,m), 4.46(1H,s) 4.57,(1H,s), 6.5-6.7(3H,m).

IRν$_{max}$$^{cm-1}$ (neat)=3300, 2950, 2920, 2850, 1460, 1380, 1200.

EXAMPLE 37

4-(3,7,11,15-Tetramethylhexadecyl)-1,3-benzenediol (Compound 37)

4-(3,7,11,15-Tetramethyl-2-hexadecenyl)-1,3-benzenediol (2.00 g: 5.14 mmole) was dissolved in ethanol (10 ml), a suspension of Raney's nickel W4 in ethanol (15 ml), was added thereto and then the mixture was reciprocatively shaken at 70° to 85° C. and a hydrogen pressure of 70 to 80 atm. for 2 days. After removing Raney's nickel by filtration, the filtrate was concentrated and the concentrate was chromatographed through a silica gel column. Thus, 1.30 g of the title compound was recovered from the fractions eluted with hexane-ethyl acetate (5:1). Yield=65%.

$^1$H NMR (200MHz,CDCl$_3$) δ=0.85(6H,d,J=6.3H$_z$), 0.87(6H,J=6.6H$_z$), 0.94(3H,d,J=6.1H$_z$), 1.0-1.8(24H$_z$,m), 2.5-2.6(2H,m), 4.95(1H,s), 5.30(1H,s), 6.3-6.5(2H,m), 6.93(1H,d,J=8.5H$_z$).

IRν$_{max}$$^{cm-1}$ (neat)=3310, 2950, 2930, 2860, 1480, 1380, 1130, 940.

TEST EXAMPLE 1

Effect on Stress Ulcer

Method

Test Animal: In the following experiments, Slc-SD straim male rats are used. They are fasted overnight before use.

Compounds to be tested (Samples): Samples were prepared by suspending each compound obtained in accordance with the foregoing method into 5% gum arabic solution.

Gastric Lesions due to Stress (Ulcer): Test was carried out according to a method disclosed in the article of K. Takagi and S. Okabe (Japan, J. Pharmacol., 1968, 18, 9-18). More specifically, test animals were placed in a stress cage (designed by the Department of Chemical Pharmacology in Tokyo Univ.) and immersed, to the level of the xiphoid processus, in a water bath maintained at 23° C. Six hours later, each animal was sacrificed by decapitation and the length of the lesions formed due to such stress was determined by examining the stomach, from which the coefficient of lesion formation (or coefficient of ulcer formation: C.L.F.) was calculated. In addition, the rate of inhibition of ulcer (%) is estimated from the following relation:

$$\frac{(C.L.F. \text{ of the control group}) - (C.L.F. \text{ of the Sample administered group})}{C.L.F. \text{ of the control group}} \times 100(\%)$$

In this connection, Samples were orally administered 15 minutes before the water immersion while 5 ml/kg of 5% gum arabic solution alone was orally administered to rats of control group.

Results

The results obtained in accordance with the aforementioned test are summarized in Table 1 given below.

TABLE 1

| Test Compound | Dose (mg/kg po) | Number of Animals | Rate of Inhibition (%) |
|---|---|---|---|
| Compound 1 | 100 | 5 | 84.9** |
| | 30 | 5 | 29.7 |
| Compound 2 | 100 | 5 | 61.1** |
| | 30 | 5 | 27.0 |
| Compound 4 | 100 | 5 | 64.3** |
| | 30 | 5 | 8.6 |
| Compound 6 | 100 | 4 | 46.5 |
| Compound 7 | 100 | 5 | 18.9 |
| Compound 8 | 100 | 5 | 61.1** |
| | 30 | 5 | 45.5 |
| Compound 9 | 100 | 5 | 57.8** |
| | 30 | 5 | 11.4 |
| Compound 10 | 100 | 5 | 37.1 |
| Compound 11 | 100 | 4 | 86.9** |
| Compound 13 | 30 | 5 | 33.6 |
| Compound 16 | 100 | 5 | 36.0 |
| Compound 17 | 100 | 5 | 89.5** |
| Compound 19 | 100 | 4 | 91.3** |
| | 30 | 5 | 51.1 |
| Compound 21 | 100 | 5 | 30.1 |
| Compound 23 | 100 | 3 | 14.0 |
| Compound 25 | 100 | 4 | 81.7** |
| Compound 26 | 100 | 5 | 72.0* |
| | 30 | 5 | 56.3* |
| Compound 27 | 100 | 5 | 70.0** |
| | 30 | 3 | 25.0 |
| Compound 28 | 100 | 5 | 91.3** |
| Compound 29 | 100 | 5 | 31.3 |
| Compound 31 | 100 | 5 | 30.7 |
| Compound 32 | 100 | 5 | 61.3 |
| Compound 33 | 100 | 5 | 19.0 |
| Compound 34 | 100 | 5 | 93.5** |
| | 30 | 4 | 20.0 |
| Compound 35 | 100 | 5 | 86.4** |
| | 30 | 4 | 38.0 |
| Compound 36 | 100 | 5 | 74.9** |
| | 30 | 5 | 69.9** |
| Compound 37 | 100 | 5 | 76.5 |
| | 30 | 5 | 68.5 |

*$P < 0.05$;
**$P < 0.01$

TEST EXAMPLE 2

Effect on Aspirin Induced Ulcers

Method

After 18 hours fasting, rats were anesthetized by ether, the pylorus was ligated and immediately thereafter Samples were administered intraduodenally (100 mg/kg). After the rats were laporotomized, aspirin (100 mg/kg) was administered orally. Four hours later, the length of gastric lesions formed was measured and the results were inspected. The calculation of the rate of inhibition was effected in the same manner as in Test Example 1.

Results and Consideration

The results obtained according to the foregoing test are summarized in Table 2 below.

TABLE 2

| Sample | Number of Animals | Rate of Inhibition (%) |
|---|---|---|
| Control | 5 | — |
| Compound 1 | 5 | 98.4** |
| Compound 4 | 5 | 87.8** |
| Compound 8 | 5 | 84.6** |
| Compound 10 | 5 | 75.2* |

*$P < 0.05$;
**$P < 0.01$

As seen from the results listed in table 2, the compounds of the present invention clearly show excellent inhibitory action against gastric lesions (or gastric ulcers) formed due to drugs (in this case aspirin) administration.

Moreover, all the compounds of this invention exhibit low toxicity and, therefore, it is not necessary to take into consideration side-effects.

The antiulcer of the present invention will hereunder be explained in more detail with reference to the following illustrative formulations.

| Formulation 1 (Soft Capsule) | |
|---|---|
| Formulation of Basic Agents (per capsule) | |
| Compound 1 | 100 mg |
| Soybean oil | 120 mg |
| | 220 mg |
| Formulation of Film (per capsule) | |
| Gelatin | 90 mg |
| conc. Glycerin | 20 mg |
| D-Sorbitol solution | 15 mg |
| Ethyl p-oxybenzoate | 0.4 mg |
| Propyl p-oxybenzoate | 0.2 mg |
| | 125.6 mg |

The foregoing components were admixed with stirring, foams present were removed by reducing the pressure to form a solution for filling capsules. Soft capsules containing, therein, 220 mg of the basic agents were prepared according to the guide (for preparing capsules) disclosed in "General Rules for Preparations" (Japanese Pharmacopoeia, 11th edition; hereunder referred to as "J.P.XI").

| Formulation 2 (Tablet) | |
|---|---|
| Effective Component (Compound 4) | 50 mg |
| Crystalline Cellulose | 50 mg |
| Corn starch | 30 mg |
| Lactose | 17.8 mg |
| Hydroxypropyl cellulose | 0.2 mg |
| Magnesium stearate | 2 mg |
| | 150.0 mg |

The foregoing components were admixed and kneaded and then dried to form granules for compressing. Tablets were prepared according to the guide (for obtaining tablets) disclosed in "General Rules for Preparations" (J.P.XI).

| Formulation 3 (Injections) | |
|---|---|
| (i) Formulation (Emulsion type injection) | |
| Effective component (Compound 8) | 25 mg |
| Soybean oil | 100 mg |
| Benzyl alcohol | 1 mg |
| Polysorbate 80 | 10 mg |
| Distilled water for injection | q.s. |
| | 5.0 ml |

The effective component, solvent and emulsifying agent were admixed and emulsified by an emulsifier. This emulsion type injection was prepared according to the guide for the preparation of injections disclosed in "General Rules for Preparations" (J.P.XI).

| (ii) Formulation (Suspension type injection) | |
|---|---|
| Effective component (Compound 9) | 25.0 mg |
| Common salt | 44.0 mg |
| Polysorbate 80 | 10.0 mg |
| Carboxymethyl cellulose | 50.0 mg |
| Distilled water for injection | q.s. |
| | 5.0 ml |

The effective component, solvent and dispersant were mixed and uniformly dispersed with a dispersing machine to form suspension type injections. These operations were carried out in accordance with the guide disclosed in "General Rules for Preparations" (J.P.XI).

| Formulation 4 (Soft Capsule) | |
|---|---|
| Formulation of Basic Agents (per capsule) | |
| Compound 11 | 200 mg |
| Soybean oil | 120 mg |
| | 320 mg |
| Formulation of Film (per capsule) | |
| Gelatin | 90 mg |
| conc. Glycerin | 20 mg |
| D-Sorbitol Solution | 15 mg |
| Ethyl p-oxybenzoate | 0.4 mg |
| Propyl p-oxybenzoate | 0.2 mg |
| | 125.6 mg |

Soft capsules containing therein 320 mg of the basic agents were prepared according to the same manner as in Formulation 1.

| Formulation 5 (Tablet) | |
|---|---|
| Effective component (compound 17) | 100 mg |
| Crystalline cellulose | 50 mg |
| Corn starch | 30 mg |
| Lactose | 17.8 mg |
| Hydroxypropyl cellulose | 0.2 mg |
| Magnesium stearate | 2 mg |
| | 200.0 mg |

The effective component, solvent and emulsifying agent were mixed and dispersed uniformly using a dispersing machine to obtain tablets in accordance with the guide disclosed in "General Rules for Preparations" (J.P.XI).

| Formulation 6 (Injections) | |
|---|---|
| (i) Formulation (Emulsion type injection) | |
| Effective component (Compound 19) | 20 mg |
| Soybean oil | 100 mg |
| Benzyl alcohol | 1 mg |
| Polysorbate 80 | 10 mg |
| Distilled water for injection | q.s. |
| | 5.0 ml |

Emulsion type injection were prepared according to the same manner as in Formulation 3(i).

| (ii) Formulation (Suspension type injection) | |
|---|---|
| Effective component (Compound 19) | 20.0 mg |
| Common salt | 44.0 mg |
| Polysorbate 80 | 10.0 mg |

| (ii) Formulation (Suspension type injection) | |
|---|---|
| carboxymethyl cellulose | 50.0 mg |
| Distilled water for injection | q.s. |
| | 5.0 ml |

Suspension type injedion were prepared according to the same manner as in Formulation 3 (ii).

As discussed and explained above in detail, according to present invention, there are, in particular, provided compounds and pharmaceuticals effective to digestive ulcers, which thus show a high therapeutic value.

What is claimed is:

1. A composition which comprises an anti-ulcer isoprenoid derivative represented by the formula (I)

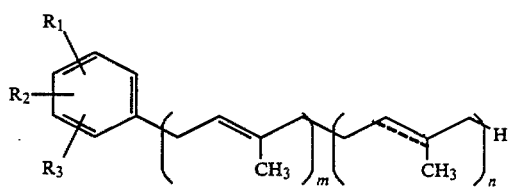

wherein $R_1$, $R_2$ and $R_3$ may be the same or different from each other and each represents a hydrogen atom or a hydroxy group and at least two of $R_1$, $R_2$ and $R_3$ represent hydroxy groups, ======= represents a single or a double bond between the carbon atoms, m represents 0 or 1 and n represents 0 or an integer of from 1 to 9 and the sum of m and n is an integer of from 1 to 9 except that when ======= represents a double bond and two of $R_1$, $R_2$ and $R_3$ are hydroxy groups and the other is a hydrogen atom, the sum of m and n is 2–8, and pharmaceutically acceptable additives.

2. The composition of claim 1 wherein the isoprenoid derivative is a compound selected from the group consisting of:

2-(3,7,11,15-Tetramethyl-2-hexadecenyl)-1,4-hydroquinone,

2-[3,7(R), 11(R), 15-Tetramethyl-2-hexadecenyl]-1, 4 hydroquinone,

2-Solanesyl-1, 4-hydroquinone, 3-(3,7,11,15-Tetramethyl-2-hexadecenyl)-1, 2-benzenediol, 4-(3,7,11,15-Tetramethyl-2-hexadecenyl)-1, 2-benzenediol, 4-(3,7,11,15-Tetramethyl-2-hexadecenyl)-1, 2, 3-benzenetriol, 4-(3,7,11,15-Tetramethyl-2-hexadecenyl)-1, 3-benzenediol, 2-(3,7,11,15-Tetramethyl-2-hexadecenyl)-1, 3, 5-benzenetriol, 2-(3,7,11,15-Tetramethylhexadecyl)-1, 4-hydroquinone, and 4-(3,7,11,15-Tetramethylhexadecyl)-1, 3-benzenediol.

3. A method comprising treating an ulcer in mammals by administering a therapeutically effective amount to treat an ulcer of an isoprenoid derivative represented by the formula (I)

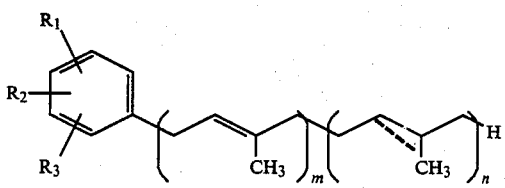

wherein $R_1$, $R_2$ and $R_3$ may be the same or different from each other and each represents a hydrogen atom or a hydroxy group and at least two of $R_1$, $R_2$ and $R_3$ represent hydroxy groups, ═══ represents a single or a double bond between the carbon atoms, m represents 0 or 1 and n represents 0 or an integer of from 1 to 9, and the sum of m and n is an integer of from 1 to 9, to said mammals.

4. The method of claim 3 wherein the isoprenoid derivative is a compound selected from the group consisting of:
2-(3,7,11,15-Tetramethyl-2-hexadecenyl)-1,4-hydroquinone, 2- Geranyl-1,4-hydroquinone,
2-Geranyl-1,3-hydroquinone,
2-[3,7(R), 11(R), 15-Tetramethyl-2-hexadecenyl]-1, 4-hydroquinone,
2-Farnesyl-1, 4-hydroquinone,
2-Geranylgeranyl-1, 4-hydroquinone,
2-(3,7,11,15,19-Pentamethyl-2,6,10,14,18-eicosapentaenyl)-1,4-hydroquinone,
2-(3,7,11,15,19,23-Hexamethyl-2,6,10,14,18,22-tetracosahexaenyl)-1, 4-hydroquinone,
2-(3,7,11,15,19,23,27-Heptamethyl-2,6,10,14,18,22,26-octacosaheptaenyl)-1, 4-hydroquinone,
2-Solanesyl-1, 4-hydroquinone,
3-(3,7,11,15-Tetramethyl-2-hexadecenyl)-1, 2-benzenediol,
4-(3,7,11,15-Tetramethyl-2-hexadecenyl)-1, 2-benzenediol,
4-(3,7,11,15-Tetramethyl-2-hexadecenyl)-1,2,3-benzenetriol,
4-(3,7,11,15-Tetramethyl-2-hexadecenyl)-1, 3-benzenediol,
2-(3,7,11,15-Tetramethyl-2-hexadecenyl)-1,3,5-benzenetriol,
2-(3,7,11,15-Tetramethylhexadecyl)-1, 4-hydroquinone, and
4-(3,7,11,15-Tetramethylhexadecyl)-1, 3-benzenediol.

5. An isoprenoid derivative represented by the formula (Ia)

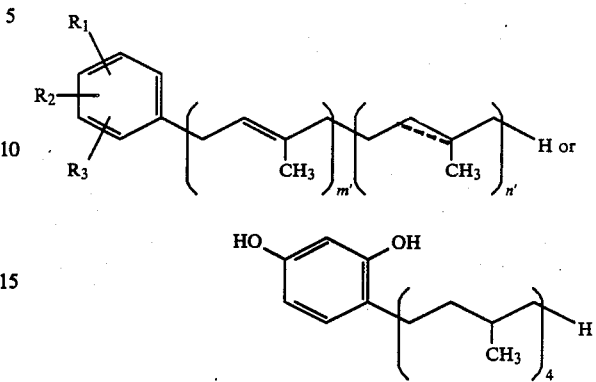

wherein $R_1$, $R_2$ and $R_3$ may be the same or different from each other and each represents a hydrogen atom or a hydroxy group provided that two or more of them do not represent hydrogen atoms at the same time, ═══ represents a single or a double bond between the carbon atoms, m' represents 1 and n' represents 3, 4 or 8 provided that ═══ represents a double bond when n' is 8 and ═══ represents a single bond when n' is 3 or 4.

6. The isoprenoid derivative of claim 5 which is 2-(3,7,11,15-Tetramethyl-2-hexadecenyl)-1, 4-hydroquinone,
2-[3,7(R), 11(R), 15-Tetramethyl-2-hexadecenyl]-1, 4-hydroquinone,
2-Solanesyl-1, 4-hydroquinone,
3-(3,7,11,15-Tetramethyl-2-hexadecenyl)-1,2-benzenediol,
4-(3,7,11,15-Tetramethyl-2-hexadecenyl)-1,2-benzenediol,
4-(3,7,11,15-Tetramethyl-2-hexadecenyl)-1,2,3-benzenetriol,
4-(3,7,11,15-Tetramethyl-2-hexadecenyl)-1, 3-benzenediol,
2-(3,7,11,15-Tetramethyl-2-hexadecenyl)-1,3,5-benzenetriol
or 4-(3,7,11,15-Tetramethylhexadecyl)-1, 3-benzenediol.

* * * * *